US008586558B2

(12) United States Patent
Isacson et al.

(10) Patent No.: US 8,586,558 B2
(45) Date of Patent: Nov. 19, 2013

(54) RAB3B FOR TREATMENT AND PREVENTION OF PARKINSON'S DISEASE

(75) Inventors: Ole Isacson, Belmont, MA (US); Chee Yeun Chung, Belmont, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 12/990,630

(22) PCT Filed: May 15, 2009

(86) PCT No.: PCT/US2009/044231
§ 371 (c)(1),
(2), (4) Date: Feb. 10, 2011

(87) PCT Pub. No.: WO2009/140649
PCT Pub. Date: Nov. 19, 2009

(65) Prior Publication Data
US 2011/0129527 A1 Jun. 2, 2011

Related U.S. Application Data

(60) Provisional application No. 61/053,914, filed on May 16, 2008.

(51) Int. Cl.
*A61K 48/00* (2006.01)
(52) U.S. Cl.
USPC ........................................ 514/44 R
(58) Field of Classification Search
USPC ........................................ 514/44 R
See application file for complete search history.

(56) References Cited

U.S. PATENT DOCUMENTS

| | | | |
|---|---|---|---|
| 5,487,739 | A | 1/1996 | Aebischer et al. |
| 5,639,275 | A | 6/1997 | Baetge et al. |
| 5,653,975 | A | 8/1997 | Baetge et al. |
| 6,027,721 | A | 2/2000 | Hammang et al. |
| 2006/0233766 | A1 | 10/2006 | Messina et al. |

FOREIGN PATENT DOCUMENTS

| WO | WO-97/44065 | 11/1997 |
|---|---|---|
| WO | WO-2006/073734 | 7/2006 |

OTHER PUBLICATIONS

Goodman & Gilman's The Pharmacological basis of Therapeutics, McGraw-Hill, New York, NY. pp. 77-101).*
Verma & Somia, (Nature 1997, 389:239-242 ).*
Verma et al (Annu Rev Biochem. 2005, 74:711-38).*
Vile et al (Gene Therapy, 2000, 7: 2-8).*
Gautam et al (Am J Respir Med, 2002; 1(1):35-46; abstract).*
Chen et al (Current Therapy, 5: (71-80), 2005).*
Deglon et al (The Journal of Gene Medicine, 7: 530-539, 2005).*
Mandel et al (Parkinson's Disease, Edited by Manuchair Ebadi and Ronald F. Pfeiffer CRC Press 2004, pp. 1-29).*
Deierborg et al (Progress in Neurobiology, 85: 407-432, 2008).*
Meissner et al (Nature Reviews, 10: 377-393, 2011).*
Gagliardi et al (ILAR Journal, 50(2): 128-143, 2009).*
Duty et al (British Journal of Pharmacology (2011) 164 1357-1391).*
Chong et al, Promoter profiling and coexpression data analysis identifies 24 novel genes that are coregulated with AMPA receptor genes, GRIAs, Genomics, 80:378-384 (2007).
Chung et al. An endogenous serine/threonine protein phosphatase inhibitor, G-substrate, reduces vulnerability in models of Parkinson's disease, J. Neurosci., 27:8314-8323 (2007).
Chung et al, Cell type-specific gene expression of midbrain dopaminergic neurons reveals molecules involved in their vulnerability and protection. Hum. Molec. Gen., 14(13):1709-1725 (2005).
Chung et al, Functional enhancement and protection of dopaminergic terminals by RAB3B overexpression, PNAS, 106(52):22474-22479 (2009).
Cooper et al., Alpha-synucieln blocks ER-Golgi traffic and Rab1 rescues neuron loss in Parkinson's models, Science, 313: 324-328 (2006).
Coppola et al, Disruption of Rab3-calmodulin interaction, but not other effector interactions, prevents Rab3 inhibition of exocytosis, EMBO J., 18: 5885-5891 (1999).
Deak et al, Rabphilin regulates SNARE-dependent re-priming of synaptic vesicies for fusion, EMBO J., 25:2856-2866 (2006).
Francis et al, Coordinate regulation of catecholamine uptake by rab3 and phosphoinositide 3-kinase, J. Biol. Chem., 277:7816-7823 (2002).
Fukuda et al, Distinct Rab binding specificity of Rim1, Rim2. rabphilin, and Noc2. Identification of a critical determinant of Rab3A/Rab27A recognition by Rim2, J. Biol. Chem., 278:15373-15380 (2003).
Gitler et al, The Parkinson's disease protein α-synuclein disrupts cellular Rab homeostasis, PNAS, 105(1):145-150 (2008).
Greene et al, Gene expression profiling of rat midbrain dopamine neurons: Implications for selective vulnerability in parkinsonism, Neurobiology of Disease, 18:19-31 (2005).
Grimm et al, Molecular basis for catecholaminergic neuron diversity, PNAS, 101(3):13891-13896 (2004).
Hioki et al, Efficient Gene Transduction of Neurons by Lentivirus with Enhanced Neuron-Specific Promoters, Gene Therapy, 14(11): 872-882 (2007).
Hovakimyan et al, Mesencephalic Human Neural Progenitor Cells Transplanted into the Neonatal Hemiparkinscnian Rat Striatum Differentiate into Neurons and Improve Motor Behavior, J. Anal., 209(6):721-732 (2006).
International Search Report and Written Opinion dated Mar. 4, 2010 for PCT Application No. PCT/US2009/044231.
Klein et al, Prevention of 6-Hydroxydopamine-Induced Rotational Behavior by BDNF Somatic Gene Transfer, Brain Res., 847(2):314-320 (1999).
Livak et al, Analysis of relative gene expression data using real-time quantitative PCR and the $2^{\Delta\Delta}$, Method. Methods. 25(4):402-408 (2001).

(Continued)

Primary Examiner — Marcia S Noble
Assistant Examiner — Magdalene Sgagias
(74) Attorney, Agent, or Firm — Nixon Peabody LLP; David S. Resnick; Leena H. Karttunen Contarino

(57) ABSTRACT

The invention features methods and compositions for the treatment and prevention of Parkinson's Disease.

6 Claims, 9 Drawing Sheets

(56) References Cited

OTHER PUBLICATIONS

Nature, Finishing the euchromatic sequence of the human genome, 431 (7011):931-945 (2004).

Niwa et al, KIF1Bβ- and KIF1A-mediated axonal transport of presynaptic regulator Rab3 occurs in a GTP-dependent manner through DENN/MADD, Nat. Cell Biol., 10:1269-1279 (2008).

Okada et al, The neuron-specific kinesin superfamily protein KIF1A is a unique monomeric motor for anterograde axonal transport of synaptic vesicle precursors, Cell, 81:769-780 (1995).

Schluter et al, A Complete Genetic Analysis of Neuronal Rab3 Function, J. Neurosci., 24(29):6629-6637 (2004).

Schulter et al, Rab3 Superprimes Synaptic Vesicles for Release: Implications for Short-Term Synaptic Plasticity, J. Neurosci., 26(4):1239-1246 (2006).

Weber et al, Distinct Functional Properties of Rab3A and Rab3B in PC12 Neuroendocrine Cells, J. Biol. Chem., 271(12):6963-6971 (1996).

Yamaguchi et al, A GDP/GTP exchange protein for the Rab3 small G protein family up-regulates a postdocking step of synaptic exocytosis in central synapses, PNAS, 99(22):14536-14541 (2002).

Zhao et al., Charcot-Marie-Tooth disease type 2A caused by mutation in a microtubule motor KIF1Bβ, Cell, 105:587-597 (2001).

Tsui et al., Functions of the nigrostriatal dopaminergic synapse and the use of neurotransplantation in Parkinson's disease, J Neurol. Aug. 2011;258(8):1393-405.

Cooper et al., Lack of functional relevance of isolated cell damage in transplants of Parkinson's disease patients, J Neurol. Aug. 2009;256 Suppl 3:310-6.

* cited by examiner

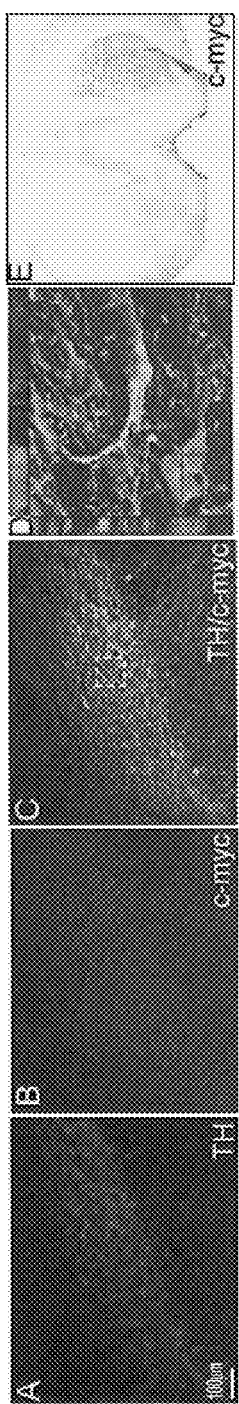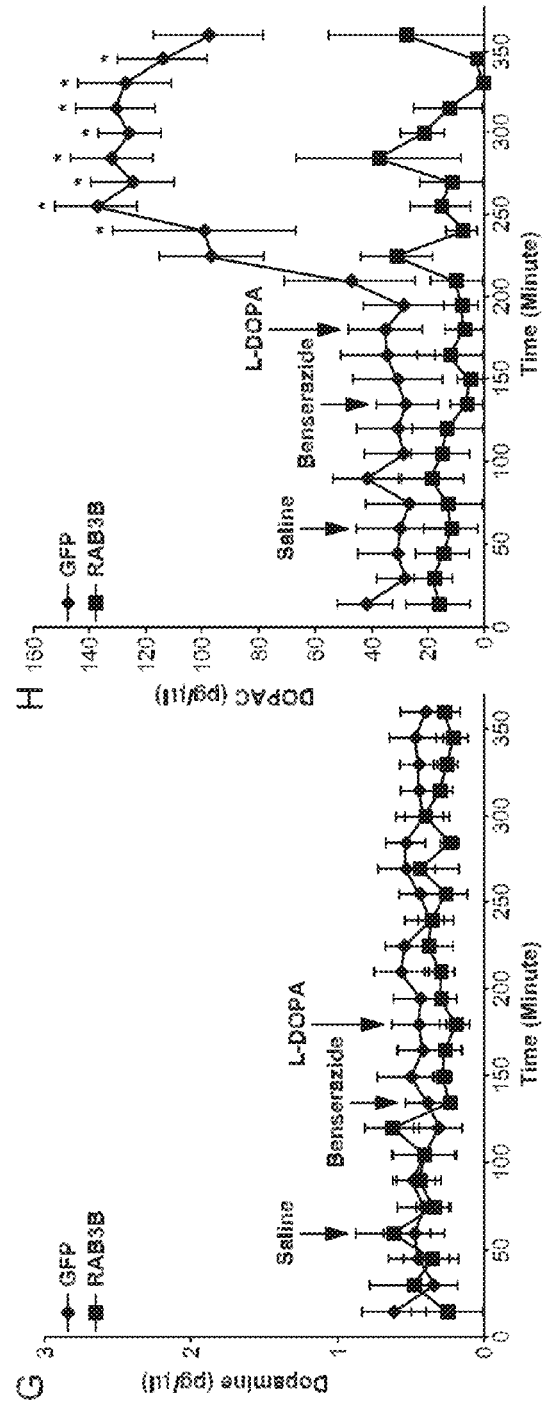
Figure 4 - (1 of 3)

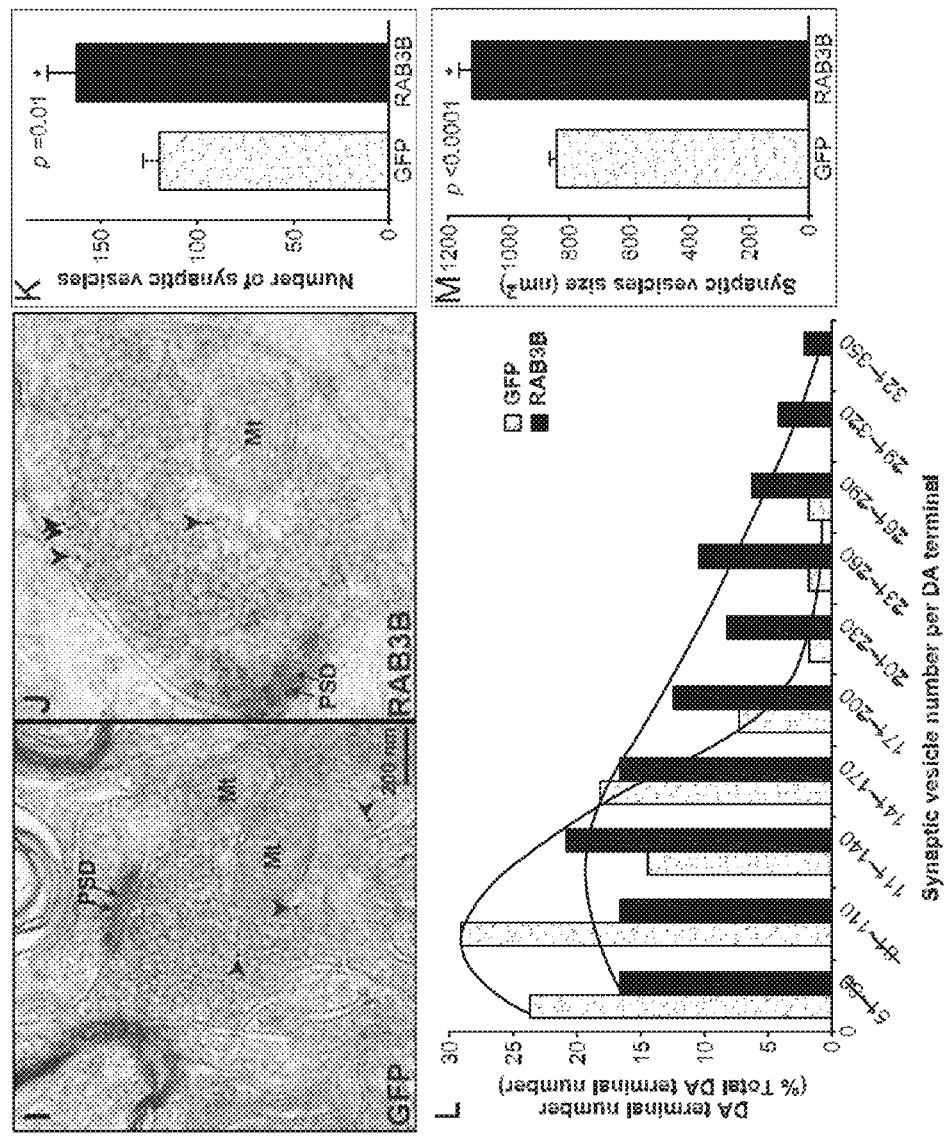
Figure 4 cont'd - (2 of 3)

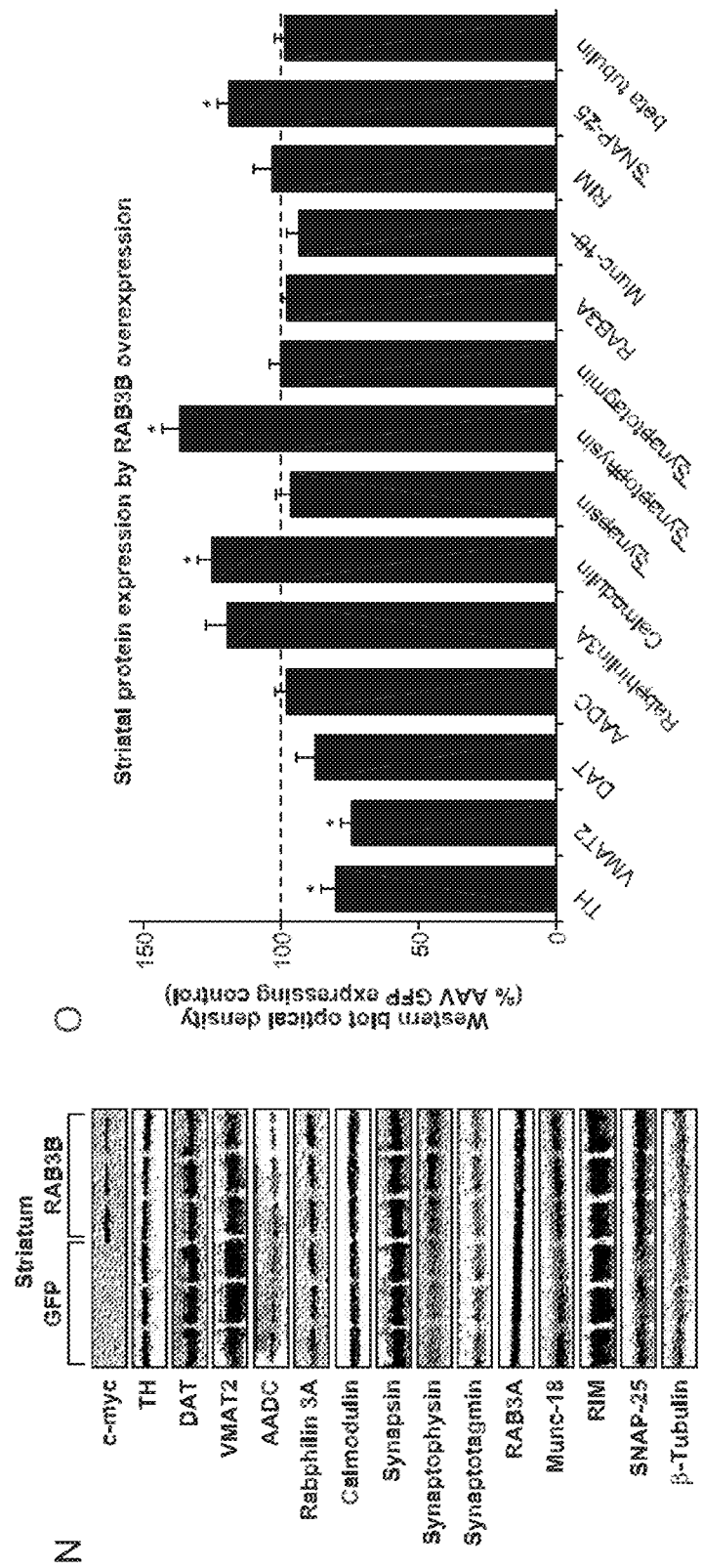
Figure 4 cont'd. - (3 of 3)

```
  1  MASVTDGKTG  VKDASDQNFD  YMFKLLIIGN  SSVGKTSFLF  RYADDTFTPA   50
 51  FVSTVGIDFK  VKTVYRHEKR  VKLQIWDTAG  QERYRTITTA  YYRGAMGFIL  100
101  MYDITNEESF  NAVQDWATQI  KTYSWDNAQV  ILVGNKCDME  EERVVPTEKG  150
151  QLLAEQLGFD  FFEASAKENI  SVRQAFERLV  DAICDKMSDS  LDTDPSMLGS  200
201  SKNTRLSDTP  PLLQQNCSC                                       219

(SEQ ID NO: 1)
```

Figure 6

```
  1 atggcttcag tgacagatgg taaaactgga gtcaaagatg cctctgacca gaattttgac
 61 tacatgttta aactgcttat cattggcaac agcagtgttg gcaagacctc cttcctcttc
121 cgctatgctg atgacacgtt caccccagcc ttcgttagca ccgtgggcat cgacttcaag
181 gtgaagacag tctaccgtca cgagaagcgg gtgaaactgc agatctggga cacagctggg
241 caggagcggt accggaccat cacaacagcc tattaccgtg gggccatggg cttcattctg
301 atgtatgaca tcaccaatga agagtccttc aatgctgtcc aagactgggc tactcagatc
361 aagacctact cctgggacaa tgcacaagtt attctggtgg ggaacaagtg tgacatggag
421 gaagagaggg ttgttcccac tgagaagggc cagctccttg cagagcagct tgggtttgat
481 ttctttgaag ccagtgcaaa ggagaacatc agtgtaaggc aggccttga gcgcctggtg
541 gatgccattt gtgacaagat gtctgattcg ctggacacag acccgtcgat gctggctcc
601 tccaagaaca cgcgtctctc ggacaccca ccgctgctgc agcagaactg ctcatgctag (SEQ ID NO: 6)
```

Figure 7

RAB3B FOR TREATMENT AND PREVENTION OF PARKINSON'S DISEASE

CROSS-REFERENCE TO RELATED APPLICATIONS

This application is the US National Phase of PCT Application No. PCT/US2009/044231, filed on May 15, 2009, which claims the benefit of U.S. Provisional Applications 61/053,914, filed May 16, 2008. All of which are hereby incorporated by reference in their entirety.

GOVERNMENT SUPPORT

This invention was made with Government support under Grant No. NS039793 awarded by the National Institutes of Health. The Government has certain rights in this invention.

BACKGROUND OF THE INVENTION

This invention relates generally to the diagnosis and treatment of neurodegenerative diseases, including Parkinson's Disease.

Parkinson's disease (PD) is a progressive neurodegenerative disease characterized clinically by bradykinesia, rigidity, and resting tremor. Selective degeneration of specific neuronal populations is a universal feature of PD that contributes to the clinical symptomology which is poorly understood. The hallmark neuropathologic feature of PD is loss of midbrain dopaminergic (DA) neurons. While the majority of PD cases are sporadic, for which a combination of environmental and genetic factors are likely responsible, familial cases that result from monogenic mutations have also been identified in genes including α-synuclein, parkin, ubiquitin C-terminal hydrolase-1, DJ-1, PINK1, and LRRK2. Regardless of specific etiology, DA neurons in the A9 region (substantia nigra pars compacta; SNc) are considerably more vulnerable than DA neurons in the immediately adjacent A10 region (ventral tegmental area; VTA). A similar pattern of differential vulnerability is observed in rodent and primate models of PD, including toxic models utilizing 6-hydroxydopamine (6-OHDA) 5 and 1-methyl 4-phenyl 1,2,3,6-tetrahydropyridine (MPTP), indicating that such differential vulnerability between A9 and A10 DA neuronal populations may be conserved between species.

It has recently been demonstrated that rodent A9 and A10 DA neurons have distinct gene expression profiles despite their many similarities (Grimm et al., Proc. Natl. Acad. Sci. USA 101: 13891-13896, 2004; Chung et al., Hum. Mol. Genet. 14: 1709-1725, 2005; Greene et al., Neurobiol. Dis. 18: 19-31, 2005). Such inherent baseline gene expression differences may create biochemical identities that underlie the different thresholds of vulnerability to pathophysiological processes. Indeed, it was recently shown that altering expression of several differentially expressed genes in cell culture did affect the vulnerability to neurotoxins.

Currently, little is known about the mechanism underlying the neurodegenerative process and the basis for its differential effects on the A9 versus the A10 dopaminergic neurons. Accordingly, disease management is largely limited to strategies that achieve symptomatic relief (e.g., by replenishing dopamine levels) rather than strategies that seek to prevent or delay neurodegeneration. Thus, better treatment methods are needed for treating and preventing neurodegenerative disorders that address the underlying molecular etiology of the disease.

SUMMARY OF THE INVENTION

This invention features a method for increasing dopaminergic neurotransmission and/or treating or preventing Parkinson's Disease (PD) in a patient by increasing the level of RAB3B or a biologically active fragment thereof, in the midbrain of that patient. In one embodiment, the level of RAB3B is increased in the midbrain dopaminergic neurons including, for example, the A9 (substantia nigra) and/or A10 (ventral tegmental area) dopaminergic neurons. The RAB3B levels may be increased by administering a vector comprising a polynucleotide encoding the RAB3B protein or biologically active fragment thereof, operably linked to at least a regulatory element, wherein the vector is taken up by the target cell (e.g., neuron or pluripotent stem cell) and the polynucleotide (and RAB3B protein) is expressed. In some embodiments, the vector is a viral vector including, for example, an adenovirus, adeno-associated virus, retrovirus, or lentivirus. The vector may be delivered to the midbrain in vivo using any suitable technique including, for example, stereotactic microinjection of the vector into or near the substantia nigra. The delivery method is designed to promote uptake and expression of the vector by the dopaminergic neurons.

In another aspect, the invention features a method for treating or preventing PD in a patient by administering, to the brain of a patient, a RAB3B protein or biologically active fragment thereof. In some embodiments, the RAB3B protein is administered by intravenous or intraventricular injection. The RAB3B protein may be soluble or may be encapsulated within a liposome. Preferably, the RAB3B protein is taken up by neurons (e.g., dopaminergic neurons, adrenergic neurons, serotonergic neurons, and/or cholinergic neurons). Alternatively, the RAB3B protein is administered to the brain of the patient by implanting cells capable of expressing a recombinant RAB3B protein. In one embodiment, the cells are autologous and are transplanted directly into the midbrain of the patient. Alternatively, the cells are derived from pluripotent stem cells, including umbilical cord blood stem cells, neuronal progenitor cells, fetal mesencephalic cells, embryonic stem cells, and postpartum derived cells (U.S. Pat. No. 5,487,739). In another embodiment, the transplanted cells are encapsulated in a permeable capsule.

In another aspect, the invention provides an isolated nucleic acid comprising a nucleotide sequence that encodes a RAB3B protein or biologically active fragment thereof and at least a regulatory element. In a related aspect, the invention provides vectors comprising such isolated nucleic acids. The RAB3B-encoding nucleic acid may be operably linked to a promoter. In some embodiments, the promoter is a neuron-specific promoter including, for example, a neuron-specific enolase promoter or a synapsin-I promoter. The vectors may be a naked DNA or a viral vector including, for example, those selected from the group of adenovirus, adeno-associated virus, retrovirus, lentivirus, and herpes simplex virus. The vectors are preferably contained in a pharmaceutically acceptable formulation including, for example, a formulation suitable for intravenous, intramuscular, intracerberoventricular, or intranigral injection. In another related aspect, the invention provides cells containing such isolated nucleic acids or vectors. In some embodiments, the cells include, for example, pluripotent stem cells, umbilical cord blood stem cells, neuronal progenitor cells, fetal mesencephalic cells, embryonic stem cells, and postpartum derived cells.

In one aspect, the invention provides a method of identifying a compound that treats or prevents Parkinson's disease in a human, involving the steps of: (a) providing cells that express RAB3B; (b) contacting the cells with a candidate compound; and (c) assessing the expression level of the genes relative to the expression level of the genes in the absence of the candidate compound, in which a candidate compound that increases the expression of said RAB3B is identified as a compound useful for treating Parkinson's disease.

In one aspect, the invention provides a method of identifying a compound for treating or preventing Parkinson's disease involving the steps of: (a) providing cells that express a reporter gene under the control of a RAB3B regulatory element; (b) contacting the cell with a candidate compound; and (c) assessing the level of expression of the reporter gene in the presence and/or absence of the candidate compound, in which a candidate compound that increases the level of expression of the reporter gene is identified as a compound that is useful for the treatment or prevention of Parkinson's disease. Any suitable reporter gene may be used. Exemplary useful reporter genes include but not limited to: glucuronidase (GUS), luciferase, chloramphenicol transacetylase (CAT), green fluorescent protein (GFP), alkaline phosphatase, and β-galactosidase.

In some embodiments of the above two aspects of the invention, contacting further includes contacting the cell with a neurotoxic compound. Exemplary neurotoxic compound includes but not limited to 1-methyl-4-phenylpyridinium (MPP+), rotenone, isoquinoline, tetrahydroisoquinoline and 6-hydroxydopamine. In some embodiments of the above two aspects of the invention, the cells are mammalian cells such as human cells or rodent cells (e.g., rat and mouse) cells, or non-human primate cells. In some embodiments of the above aspects of the invention, the cells may be neuronal cells. The cells may be immortalized cells or they may be derived from cultured primary cells (e.g., cultured embryonic ventral mesencephalon cells). Useful immortalized cells include, for example, PC12 cells. Desirably, the PC12 cells also recombinantly express RAB3B. In some embodiments of the above aspects of the invention, the assessing step (c) includes measuring the level of RAB3B RNA.

By "RAB3B" is meant a protein having an amino acid sequence substantially identical to the human RAB3B sequence of SEQ ID NO.: 1, and biologically active fragments thereof. A suitable cDNA encoding RAB3B is provided at GenBank Accession No. AF498932 (FIG. 7; SEQ ID NO: 6).

By "biologically active RAB3B fragment" is meant any protein or polypeptide that is substantially identical to a portion of SEQ ID NO: 1 and possesses at least one biological activity of RAB3B. In preferred embodiments, the RAB3B fragment contains at least one (and preferably two or three) of the GTP binding domains corresponding to amino acids 29-36 (SEQ ID NO: 2), 77-81 (SEQ ID NO: 3), and 135-138 (SEQ ID NO: 4) of the human RAB3B protein. In other embodiments, the RAB3B fragment contains the effector binding domain corresponding to amino acids 51-59 (SEQ ID NO: 5) of the human RAB3B protein. Accordingly, some specific biologically active RAB3B fragments include, for example, polypeptides containing amino acids 29-59, 29-81, 29-138, 29-188, 51-81, 51-138, and 51-188. In preferred embodiments, the RAB3B fragment is about 30, 40, 50, 60, 70, 80, 90, 100, 120, 140, 160, 180, or more amino acids in length.

By "RAB3B biological activity" is meant any biological activity associated with the full length native RAB3B protein. In preferred embodiments, RAB3B biological activity refers to a GTPase activity (i.e., the ability to hydrolyse the γ-phosphate of GTP, producing GDP). Other RAB3B biological activities include the ability to bind accessory proteins including, for example, p85 and phosphoinositide 3-kinase (PI3K).

By "treating" is meant administering a pharmaceutical composition for the purpose of improving the condition of a patient by reducing, alleviating, or reversing at least one adverse effect or symptom.

By "preventing" is meant identifying a subject (i.e., a patient) having an increased susceptibility to PD but not yet exhibiting symptoms of the disease and administering a therapy according to the principles of this disclosure. The preventive therapy is designed to reduce the likelihood that the susceptible subject will later become symptomatic or that the disease will be delay in onset or progress more slowly than it would in the absence of the preventive therapy.

A subject may be identified as having an increased likelihood of developing PD by any appropriate method including, for example, by identifying a family history of PD or other degenerative brain disorder.

By a "therapeutically effective amount" is meant a quantity of compound (e.g., a RAB3B protein or biologically active fragment thereof) delivered with sufficient frequency to provide a medical benefit to the patient. Thus, a therapeutically effective amount of a protein is an amount sufficient to treat or ameliorate a symptom of PD.

By a "vector" is meant a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory element and may control the transcription of the nucleic acid sequence of interest. As used herein, a vector need not be capable of replication in the ultimate target cell or subject. The term vector may include expression vector and cloning vector.

Suitable expression vectors are well-known in the art, and include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

By a "regulatory element" is meant a nucleic acid sequence capable of modulating the transcription of a gene. Non-limiting examples of regulatory element include promoter, enhancer, silencer, poly-adenylation signal, transcription termination sequence. Regulatory element may be present 5' or 3' regions of the native gene, or within an intron.

By a "promoter" is meant a nucleic acid sequence sufficient to direct transcription of a gene. Also included in the invention are those promoter elements which are sufficient to render promoter dependent gene expression controllable for cell type specific, tissue specific or inducible by external signals or agents By a "neuron-specific promoter" is meant a promoter that results in a higher level of transcription of a gene in cells of neuronal lineage compared to the transcription level observed in cells of a non-neuronal lineage.

By "operably linked" is meant that a nucleic acid molecule and one or more regulatory sequences (e.g., a promoter) are connected in such a way as to permit expression and/or translation of the product (e.g., a protein) of the nucleic acid molecule when the appropriate molecules (e.g., transcriptional activator proteins) are bound to the regulatory sequences.

By "isolated nucleic acid molecule," or "substantially pure nucleic acid is meant a nucleic acid molecule that is removed from its naturally-occurring position in the human genome. The term includes, for example, a recombinant DNA that is incorporated into a vector or an autonomously replicating plasmid or virus.

By "substantially identical", when referring to a protein or polypeptide, is meant one that has at least 80%, 85%, 90%, 95%, or 99% sequence identify to a reference amino acid sequence. The length of comparison is preferably the full length of the polypeptide or protein, but is generally at least 10, 15, 20, 25, 30, 40, 50, 60, 80, or 100 or more contiguous amino acids. A "substantially identical" nucleic acid is one that has at least 80%, 85%, 90%, 95%, or 99% sequence identify to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

BRIEF DESCRIPTION OF THE DRAWINGS

FIGS. 1A-1F show the location of RAB3 protein expression in the rat striatum by immunohistochemical staining FIGS. 1A and 1D show RAB3A expression was evenly distributed throughout the striatum including TH positive fibers (A: 25× magnification and D: 100× magnification). FIGS. 1B, 1C, 1E, and 1F show the expression of RAB3B was enriched in rat VTA (A10) DA projection area and co-localized with TH including ventromedial striatum (FIG. 1B: 25× magnification and FIG. 1E: 100× magnification) and the septum (FIG. 1F: 100× magnification). Co-localization of RAB3B and TH was confirmed by Z-stack confocal image (FIG. 1C). FIGS. 1G, 1H and 1I show the SN (A9) and VTA (A10) DA neurons collected from fresh frozen human midbrain using laser capture microdissection (LCM). DA neurons were labeled using TH staining (FIG. 1G). TH-positive cells were targeted for LCM with a 7.5 μm laser diameter (FIG. 1H). Captured cells on the thermoplastic film were visualized before processing for RNA extraction (FIG. 1I). FIG. 1J shows that RAB3B mRNA was expressed at more than 10-fold higher levels in the human VTA (A10) compared to the SN (A9) midbrain region. RAB3A and RAB3C were expressed in approximately equal amounts in these brain regions. Data are shown as mRNA ratios of A9/A10 DA neurons±SEM (n=4 human male and n=4 human female).

FIGS. 2E and 2F show the effect of knock-down of the endogenous RAB3A or RAB3B using siRNA. Cell viability was measured using the MTS assay and results are expressed as a percentage of cells exposed to control siRNA without 6-OHDA treatment. The endogenous RAB3B knock-down increased vulnerability of the cells to 6-OHDA toxicity (FIG. 2E) and MG-132 toxicity (FIG. 2F). Data are shown as means±SEM (n=6-8) and are representatives of three or more experiments with the similar trends. (§; $p<0.001$, Two way ANOVA, *; $p<0.01$, One way ANOVA, Tukey test).

FIGS. 3A and 3B are a series of bar graphs showing that overexpression of RAB3B increases [$^3$H]-dopamine (DA) uptake by M17 cells. Nomifensine, a dopamine transporter (DAT) blocker was used to calculate the DAT-dependent specific [$^3$H]-DA uptake (FIG. 3A), and reserpine, a vesicular monoamine transporter 2 (VMAT2) blocker was used to calculate the VMAT2-dependent specific [$^3$H]-DA uptake (FIG. 3B). Data are shown as means±SEM (n=4*; $p<0.01$, two tail test). FIG. 3C shows neurotransmitter content as determined in GFP or RAB3B overexpressing BE(2)-M17 cells by HPLC analysis. RAB3B overexpression significantly increased DA, noradrenaline and 5-HT contents compared to GFP overexpression. Data are shown as means±SEM (n=5, *, $p<0.01$, two tail t-test). FIGS. 3D and 3E show a Western blot, and its quantification respectively, demonstrating that RAB3B overexpression in BE(2)-M17 cells causes a compensatory reduction of synaptotagmin and RAB3A levels, while increasing levels of calmodulin (a RAB3B effector protein), synaptophysin, and SNAP-25. Optical densities of the individual bands were quantified using NIH image. Optical densities of RAB3B overexpressing conditions were normalized by the averaged value of GFP expressing condition. Data are shown as mean±SEM (GFP, n=4; RAB3B, n=4; *, $p<0.05$ two tail t-test).

FIG. 4 shows that RAB3B overexpression in vivo increases DA content, the number and the size of synaptic vesicles and levels of presynaptic proteins. AAV2 RAB3B$^{c-myc}$ injection into the SN resulted in very efficient transduction of DA neurons (FIG. 4A-C) and their projection target, striatum (FIG. 4E) detected by an antibody against c-myc. FIG. 4D is the z-stack image of the perforated square in FIG. 4C confirming co-localization of TH/c-myc. Three weeks after injection, GFP or RAB3B overexpressing striata were dissected for HPLC analysis. A significant increase in DA content was measured in the RAB3B overexpressing striatum compared to the GFP expressing striatum. Ratios of DA metabolites to DA, however, remain unchanged in the RAB3B overexpressing striatum (FIG. 4F). Data are shown as means±SEM (AAV GFP, n=8; AAV RAB3B$^{c-myc}$, n=8; *$p<0.05$ two tail t-test). Extracellular DA and DOPAC levels were measured in the striatum of GFP or RAB3B overexpressing rats before and after 50 mg/kg L-DOPA administration using microdialysis. There was no difference in baseline extracellular DA levels between GFP and RAB3B overexpressing conditions. L-DOPA administration at this dose did not alter DA levels (FIG. 4G). DOPAC levels were dramatically increased after L-DOPA injection in GFP overexpressing striatum whereas they remain unaltered in the RAB3B overexpressing striatum (FIG. 4H). Data are shown as mean±SEM (GFP, n=6; RAB3B, n=5; *p<0.05 two tail t-test). FIG. 4I-M: The number and the size of synaptic vesicles were quantified in GFP or c-myc (RAB3B)-positive presynaptic terminals identified by immunogold technique (FIG. 4I and FIG. 4J). Vesicle number was determined by counting all vesicles contained in the individual presynaptic terminal (73 terminals for GFP and 85 terminals for RAB3B expressing conditions). RAB3B-positive terminals possessed the greater number of synaptic vesicles than GFP-positive terminals when averaged (FIG. 4K). More RAB3B-positive terminals tend to have the higher number of synaptic vesicles when sorted by the number of synaptic vesicles (FIG. 4L). Average vesicle size of a single presynaptic terminal was determined using fractionator and nucleator function in Stereoinveistigator software (Microbrightfield). RAB3B-positive terminals contained significantly larger vesicles compared to GFP-positive terminals (FIG. 4M). Western blot analysis revealed that TH, VMAT2 levels were significantly reduced whereas calmodulin, synaptophysin and SNAP-25 levels were increased (FIG. 4N and FIG. 4O). Optical densities of the individual bands were quantified using NIH image. Optical densities of RAB3B overexpressing conditions were normalized by the averaged value of GFP expressing condition. Data are shown as mean±SEM (GFP, n=4; RAB3B, n=4; *p<0.05 two tail t-test).

FIG. 6 provides the amino acid sequence of human RAB3B (SEQ ID NO: 1).

FIG. 7 provides a cDNA sequence encoding human RAB3B (SEQ ID NO: 6)

DETAILED DESCRIPTION

Figure 1:
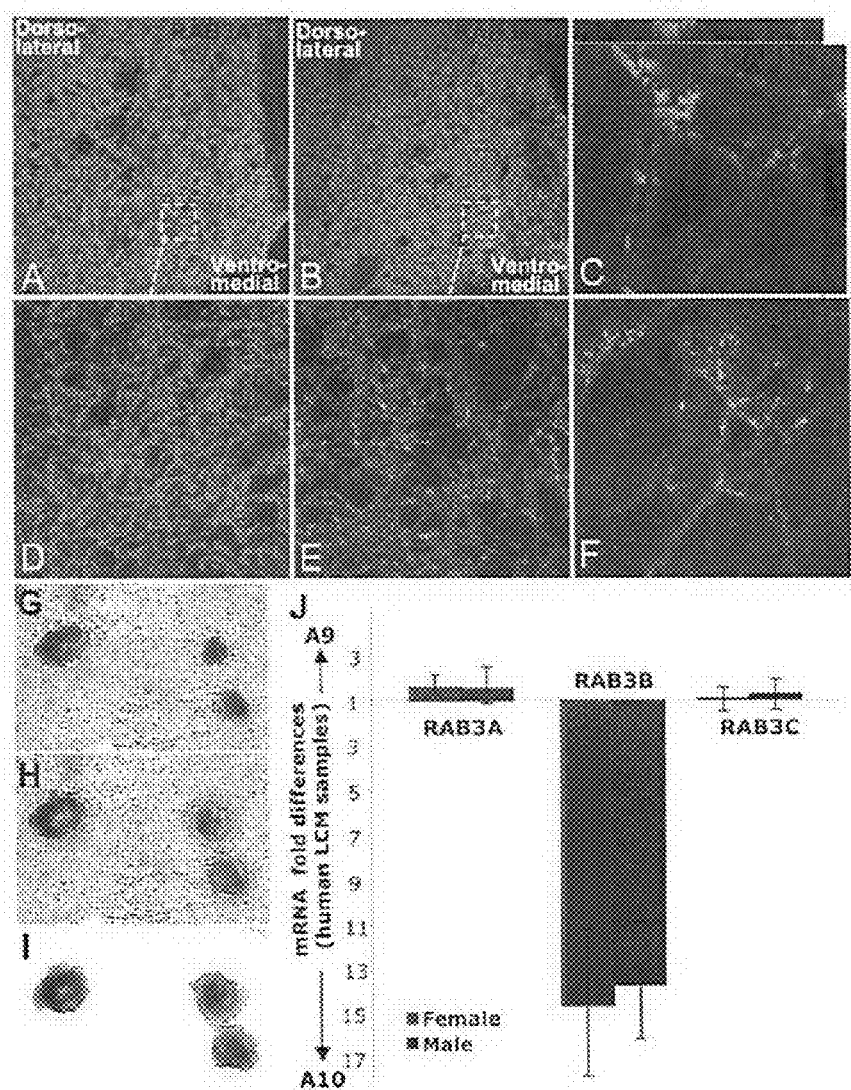
FIG. 1 shows that the RAB3 expression is elevated in VTA (A10) DA terminals in rat and RAB3B mRNA is elevated in VTA (A10) DA neurons in human.

The methods and compositions of this invention are based on the discovery that an elevated RAB3B level is neuroprotective of dopaminergic neurons. RAB3B overexpression in A9 dopaminergic (DA) neurons resulted in an increase in the striatal DA content and in the expression levels of RAB3 effector proteins calmodulin, synaptophysin, and dynein.

Overexpression of RAB3B in dopaminergic neuroblastoma cell line, BE(2)-M17 cells was protective against 6-OHDA (an oxidative stressor) and MG132 (a proteasome inhibitor) induced toxicity whereas RAB3A was protective only against MG-132 toxicity. On the other hand, reduction of endogenous RAB3B using small interfering RNA (siRNA) increased the vulnerability of the cells to both toxins demonstrating that endogenous RAB3B confers protection against these insults. Protection against 6-OHDA toxicity appeared to be specific to RAB3B, and not RAB3A, indicating distinct functions for different RAB3 isoforms.

RAB3B overexpression in vivo is protective against a retrograde 6-OHDA lesion in rats. RAB3B overexpressing rats showed increased behavioral performance relative to the control group. Postmortem analysis, stereological counting of TH-positive neurons showed that there were significantly more TH-positive neurons remaining in the RAB3B overexpressing SN compared to the GFP overexpressing SN after the 6-OHDA lesion. Protection of SN (A9) DA neurons by RAB3B was also confirmed by increased DA content and reduced DA turnover in the RAB3B overexpressing striatum.

Overexpression of RAB3B resulted in a significant increase in striatal DA content without changing the DA turnover rate, determined by ratios of dopamine metabolites (DOPAC, HVA and 3-MT) to DA. Challenging with L-DOPA administration using microdialysis, showed no increase in baseline DA levels with or without intraperitoneal injection of L-DOPA in RAB3B overexpressing striatum. However, L-DOPA administration induced a marked increase in DOPAC levels from the baseline in the control striatum. In contrast, this surge of DOPAC increase was abolished in the RAB3B overexpressing striatum. This is most likely due to the instant metabolism of the suddenly increased cytosolic DA to DOPAC by monoamine oxidase (MAO) in the cells, which would be diffused out to extracellular space. Furthermore, RAB3B overexpression alters synaptic vesicle dynamics at presynaptic DA terminals, resulting in increased number and size of synaptic vesicles and increased DA content in the striatum.

Accordingly, Parkinson's Disease (PD), a human disease characterized primarily by a loss of dopaminergic neurons particularly in the A9 midbrain region, can be treated or prevented by increasing the expression or activity of RAB3B.

RAB3B Protein

RAB proteins are monomeric GTPase proteins and form the largest family of the Ras superfamily of GTPases. They are localized to the cytoplasmic face of vesicles and organelles, including the endoplasmic reticulum and golgi apparatus. They are recognized for their key roles in both vesicle transport and fusion. Among these, RAB3 proteins (RAB3A-D) are enriched in synaptic vesicles in neurons and modulating the vesicle trafficking at the synaptic terminals. They facilitate neurotransmitter secretion by regulating the assembly, fusion and recycling of synaptic vesicles in concert with a complex of SNARE proteins including synaptobrevin, syntaxin 1 and SNAP-25, and effector proteins including RIM and rabphilin 3 (Coppola et al., EMBO J., 18: 5885-91, 1999; Deak et al., EMBO J., 25: 2856-66, 2006; Fukuda et al., J. Biol. Chem., 278: 15373-15380, 2003). In addition to this well-understood role of RAB3 on synaptic vesicle fusion at the synaptic terminal, RAB3 may function in vesicle transport to the synaptic terminal by interacting with specific motor proteins (Niwa et al., Nat. Cell Biol., 10: 1269-1279, 2008). It has been recently demonstrated that RAB3 co-immunoprecipitates with KIF1A which, together with KIF1B, is a kinesin-like motor proteins known to transport synaptic vesicles (Okada et al., Cell, 81: 769-780, 1995; Zhao et al., Cell, 105: 587-597, 2001).

Yeast genome-wide screening studies report that distinct groups of genes modified the toxicity caused by α-synulcein compared to mutant huntingtin. The modifiers for α-synulcein toxicity belongs to the genes related to the vesicle-mediated transport including RAB proteins as well as the lipid metabolism genes. In addition, recent study reported that α-synulcein blocks ER-golgi transport and overexpressing RAB1 protein rescues dopaminergic neurons from α-synulcein mediated toxicity in c-elegance, yeast, drosophila, and rat ventral mesencephalic culture (Cooper et al., Science, 313: 324-328, 2006). In addition to ER-golgi transport problems, several studies suggest a role for α-synulcein in maintaining synaptic vesicle and neurotransmitter release at the synaptic terminal. This suggests that α-synulcein may disturb Golgi to synaptic vesicle or plasma membrane transport as well.

RAB3B Regulatory Element

Exemplary regulatory element for RAB3B gene can be found upstream of the first start codon of RAB3B gene in human chromosome 1. In one embodiment, one of such RAB3B regulatory element can be within 100 bases, within 250 bases, within 500 bases, within 750 bases upstream of nucleotide position 52157420 of human chromosome 1 (GenBank Accession number: NC_000001; Nature, 431 (7011): 931-945, 2004). In another embodiment, one of such RAB3B regulatory element can be within 1 kb, within 2 kb, within 5 kb, within 10 kb, within 25 kb, within 50 kb, within 75 kb or within 100 kb upstream of nucleotide position 52157420 of human chromosome 1 (GenBank Accession number: NC_000001; Nature, 431 (7011): 931-945, 2004).

In one embodiment, a useful RAB3B regulatory element may comprise a cyclic-AMP response element like sequence: 5'-TGACATAA-3' (SEQ ID NO: 10). In another embodiment, RAB3B regulatory element may comprise a sequence 5'-RGGCGGGNY-3' (SEQ ID NO: 11). In another embodiment, RAB3B regulatory element may comprise a sequence 5'-RGGCGKGGC-3' (SEQ ID NO: 7).

Vectors Suitable for Delivery to Humans

This invention features methods and compositions for treating or preventing PD. In one aspect, the invention features methods of gene therapy to express RAB3B in the midbrain, preferably the dopaminergic neurons of the midbrain, of a patient. Gene therapy, including the use of viral vectors as described herein, seeks to transfer new genetic material (e.g., polynucleotides encoding RAB3B) to the cells of a patient with resulting therapeutic benefit to the patient. For in vivo gene therapy, expression vectors encoding the gene of interest is administered directly to the patient. The vectors are taken up by the target cells (e.g., neurons or pluripotent stem cells) and the RAB3B gene expressed. Recent reviews discussing methods and compositions for use in gene therapy include Eck et al., in Goodman & Gilman's The Pharmacological Basis of Therapeutics, Ninth Edition, Hardman et al., eds., McGray-Hill, New York, 1996, Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions.

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; genetically modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al., Med Sci Monit. 11: RA110-121, 2005).

Retroviruses are also useful as gene therapy vectors and usually (with the exception of lentiviruses) are not capable of transfecting non-dividing cells. The invention includes use of any appropriate type of retrovirus that is known in the art, including, but not limited to, HIV, SIV, FIV, EIAV, and Moloney Murine Leukaemia Virus (MoMLV). Typically, therapeutically useful retroviruses including deletions of the gag, pol, or env genes.

In another aspect, the invention features the methods of gene therapy that utilize a lentivirus vectors to express RAB3B in a patient. Lentiviruses are a type of retroviruses with the ability to infect both proliferating and quiescent cells. An exemplary lentivirus vector for use in gene therapy is the HIV-1 lentivirus. Previously constructed genetic modifications of lentiviruses include the deletion of all protein encoding genes except those of the gag, pol, and rev genes (Moreau-Gaudry et al., Blood. 98: 2664-2672, 2001).

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al., Biochem J. 387: 1-15, 2005; U.S. Patent Publication 2006/0204519).

Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in gene therapy include parainfluenza viruses, poxviruses, and alphaviruses, including Semliki forest virus, Sinbis virus, and Venezuelan equine encephalitis virus (Kennedy, Brain. 120: 1245-1259, 1997).

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff, et al., Human Mol. Genet., 1:363-369, 1992; Wolff, et al., Science, 247, 1465-1468, 1990. DNA-mediated gene transfer has also been characterized in liver, heart, lung, brain and endothelial cells. See Zhu, et al., Science, 261: 209-211, 1993; Nabel, et al., Science, 244:1342-1344, 1989. DNA for gene transfer also may be used in association with various cationic lipids, polycations and other conjugating substances. See Przybylska et al., J. Gene Med., 6: 85-92, 2004; Svahn, et al., J. Gene Med., 6: S36-S44, 2004.

Methods of gene therapy using cationic liposomes are also well known in the art. Exemplary cationic liposomes for use in this invention are DOTMA, DOPE, DOSPA, DOTAP, DC-Chol, Lipid GL-67™, and EDMPC. These liposomes may be used in vivo or ex vivo to encapsulate a RAB3B vector for delivery into target cells (e.g., neurons or pluripotent stem cells).

Typically, vectors made in accordance with the principles of this disclosure will contain regulatory elements that will cause constitutive expression of the RAB3B coding sequence. Desirably, neuron-specific regulatory elements such as neuron-specific promoters are used in order to limit or eliminate ectopic RAB3B expression in the event that the vector is incorporated into cells outside of the target region. Several regulatory elements are well known in the art to direct neuronal specific gene expression including, for example, the neural-specific enolase (NSE), and synapsin-1 promoters (Morelli et al. J. Gen. Virol. 80: 571-583, 1999).

Transplantation of Modified Neuronal or Progenitor Cells

In another aspect of the invention, ex vivo gene therapy is used to effect RAB3B expression in the midbrain of a patient. Generally, this therapeutic strategy involves using the expression vectors and techniques described above to transfect cultured cells in vitro prior to implantation of those cells into the brain (i.e., the midbrain) of a patient. The advantage of this strategy is that the clinician can ensure that the cultured cells are expressing suitable levels of RAB3B in a stable and predictable manner prior to implantation. Such preliminary characterization also allows for more precise control over the final dosage of RAB3B that will be expressed by the modified cells.

In one embodiment, autologous cells are isolated, transfected, and implanted into the patient. The use of autologous cells minimizes the likelihood of rejection or other deleterious immunological host reaction. Other useful cell types include, for example, pluripotent stem cells, including umbilical cord blood stem cells, neuronal progenitor cells, fetal mesencephalic cells, embryonic stem cells, and postpartum derived cells (U.S. Patent Application 2006/0233766). In another embodiment, cells are encapsulated in a semipermeable, microporous membrane and transplanted into the patient adjacent to the substantia nigra (WO 97/44065 and U.S. Pat. Nos. 6,027,721; 5,653,975; 5,639,275). The encapsulated cells are modified to express a secreted version of RAB3B which provides therapeutic benefit to the surrounding brain regions.

Cell transplantation therapies typically involve grafting the RAB3B-expressing replacement cell populations into the lesioned region of the nervous system (e.g., the A9 region of the substantia nigra), or at a site adjacent to the site of injury. Most commonly, the therapeutic cells are delivered to a specific site by stereotaxic injection. Conventional techniques for grafting are described, for example, in Bjorklund et al. (Neural Grafting in the Mammalian CNS, eds. Elsevier, pp 169-178, 1985), Leksell et al. (Acta Neurochir., 52:1-7, 1980) and Leksell et al. (J. Neurosurg., 66:626-629, 1987). Identification and localization of the injection target regions will generally be done using a non-invasive brain imaging technique (e.g., MRI) prior to implantation (see, for example, Leksell et al., J. Neurol. Neurosurg. Psychiatry, 48:14-18, 1985).

Briefly, administration of cells into selected regions of a patient's brain may be made by drilling a hole and piercing the dura to permit the needle of a microsyringe to be inserted. Alternatively, the cells can be injected into the brain ventricles or intrathecally into a spinal cord region. The cell preparation of the invention permits grafting of the cells to any predetermined site in the brain or spinal cord. It also is possible to effect multiple grafting concurrently, at several sites, using the same cell suspension, as well as mixtures of cells.

Following in vitro cell culture and isolation as described herein, the cells are prepared for implantation. The cells are suspended in a physiologically compatible carrier, such as cell culture medium (e.g., Eagle's minimal essential media), phosphate buffered saline, or artificial cerebrospinal fluid (aCSF). Cell density is generally about $10^7$ to about $10^8$ cells/ml. The volume of cell suspension to be implanted will vary depending on the site of implantation, treatment goal, and cell density in the solution. For the treatment of Parkinson's Disease, about 30-100 µl of cell suspension will be administered in each intra-nigral or intra-putamenal injection and each patient may receive a single or multiple injections into each of the left and right nigral or putaminal regions.

In some embodiments, the RAB3B-expressing cells are encapsulated within permeable membranes prior to implantation. Encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW ~200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off ~40-80 kDa).

Synthesis of RAB3B Proteins

Nucleic acids that encode a RAB3B protein or fragment thereof may be introduced into various cell types or cell-free systems for expression, thereby allowing purification of the RAB3B protein for large-scale production and patient therapy.

Eukaryotic and prokaryotic RAB3B expression systems may be generated in which a RAB3B gene sequence is introduced into a plasmid or other vector, which is then used to transform living cells. Constructs in which the RAB3B cDNA contains the entire open reading frame inserted in the correct orientation into an expression plasmid may be used for protein expression. Prokaryotic and eukaryotic expression systems allow for the RAB3B protein to be recovered, if desired, as fusion proteins or further containing a label useful for detection and/or purification of the RAB3B protein. Typical expression vectors contain regulatory elements that direct the synthesis of large amounts of mRNA corresponding to the inserted RAB3B nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as Escherichia coli, requires the insertion of the RAB3B nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Stable or transient cell line clones of mammalian cells can also be used to express a RAB3B protein. Appropriate cell lines include, for example, COS, HEK293T, CHO, or NIH cell lines.

Once the appropriate expression vectors containing a RAB3B gene, fragment, fusion, or mutant are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. In vitro expression of a RAB3B protein, fusion, polypeptide fragment, or mutant encoded by cloned DNA may also be used. Those skilled in the art of molecular biology will understand that a wide variety of expression systems and purification systems may be used to produce recombinant RAB3B proteins and fragments thereof.

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Pharmaceutical Compositions

The present invention includes the administration of RAB3B, and biologically active fragments thereof, for the treatment or prevention of PD. The administration of RAB3B, regardless of its method of manufacture, will be in an amount, frequency, and duration sufficient to ameliorate at least one symptom of PD. The symptoms of PD that may be ameliorated include, for example, phenotypic symptoms (e.g., resting tremor) or neuroanatomical symptoms (e.g., protecting or restoring midbrain dopaminergic neurons).

The therapeutic molecules of this invention can be administered to a subject, e.g., a human, alone or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. Exemplary pharmaceutically acceptable carriers include physiological saline and artificial cerebrospinal fluid (aCSF). Other physiologically acceptable carriers and their formulations are known to one skilled in the art and described, for example, in Remington: The Science and Practice of Pharmacy, (21st edition), 2005, Lippincott Williams & Wilkins Publishing.

Pharmaceutical formulations of a therapeutically effective amount of a compound of the invention, or pharmaceutically acceptable salt-thereof, can be administered parenterally (e.g. intramuscular, intraperitoneal, intravenous, or subcutaneous injection), or by intrathecal or intracerebroventricular injection in an admixture with a pharmaceutically acceptable carrier adapted for the route of administration.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The protein or therapeutic compound of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

Identification of Candidate Compounds Useful for Treating or preventing Parkinson's Disease A candidate compound that is beneficial for treating or preventing PD can be identified using the methods of this invention. A candidate compound can be identified for its ability to increase the expression or biological activity of RAB3B gene. Candidate compounds that modulate the expression level or biological activity of the polypeptide of the invention by at least 10%, 20%, 30%, 40%, 50%, 60%, 70%, 80%, 90%, 95%, 100%, or more relative to an untreated control not contacted with the candidate compound are identified as compounds useful for treating and preventing PD.

Screening Assay Using Cells Expressing RAB3B

A wide array of cell types, may be used in the screening methods of this invention to identify candidate compounds for the treatment of PD by assessing the effects of the candidate compounds on the expression of RAB3B. Primary fetal dopaminergic neurons or cell lines exhibiting some characteristics of the dopaminergic neuronal phenotype may be used in the present invention. Cell lines have the advantage of providing a homogeneous cell population, which allows for reproducibility and sufficient number of cells for experiments. Primary dopaminergic cultures are derived from tissues harvested from developing ventral mesencephalon (VM) containing the substantia nigra. They have the advantage of containing authentic dopaminergic neurons cultured in a context of their naturally occurring neighboring cells. Human Dopaminergic Neuron Precursor (DAN) cells may be used to screen the candidate compounds.

Alternatively, vectors comprising RAB3B coding sequence operably linked to at least one regulatory element may be introduced into the cells. Vectors encoding RAB3B nucleic acid sequence may further comprise non-RAB3B nucleic acid sequence which may be co-expressed with RAB3B as a fusion product or as a co-transcript. Non limiting examples of such non-RAB3B nucleic acid sequence includes His-tag (a stretch of poly histidines), FLAG-tag, and Green Fluorescent Protein (GFP). His-tag and FLAG-tag can be used to in many different methods, such as purification of RAB3B protein. The tags can also serve as an important site for antibody recognition.

Exemplary, eukaryotic vectors, include the cloned bovine papilloma virus genome, the cloned genomes of the murine retroviruses, and eukaryotic cassettes, such as the pSV-2 gpt system [described by Mulligan and Berg, Nature Vol. 277: 108-114 (1979)] the Okayama-Berg cloning system [Mol. Cell. Biol. Vol. 2:161-170 (1982)], and the expression cloning vector described by Genetics Institute (Science. 1985; 228: 810-815), pCMV Sport, pCDNA™ 3.3 TOPO®, BaculoDirect™ Baculovirus Expression System (Invitrogen Corp., Carlsbad, Calif., USA), StrataClone™ (Stratagene, Calif., USA), pBAC vectors (EMD Chemicals Inc, NJ, USA).

Expression of RAB3B RNA may be assessed by microarray such as by Affymetrix GeneChip® technology, or by Northern blot analysis (Sambrook, et al., Molecular Cloning: A Laboratory Manual (1989), Second Edition, Cold Spring Harbor Press, Plainview, N.Y.). The RAB3B polypeptide may be detected by immunological methods (e.g., ELISA, RIA, Western blot). Methods for screening a candidate compound can also be found in U.S. Application Publication 2006/0078890. The contents of which are incorporated herein to its entirety.

Reporter Gene Assays

Expression of a reporter gene that is operably linked to at least a RAB3B regulatory element can be used to identify a candidate compound for treating or preventing PD. Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. A genomic DNA fragment carrying at least a RAB3B regulatory element (e.g., a promoter and/or enhancer) is first cloned using standard approaches (such as those described by Sambrook et al. (supra)). The DNA carrying at least one RAB3B regulatory element is then inserted, by DNA subcloning, into a reporter vector, thereby placing a vector-encoded reporter gene under the control of RAB3B regulatory element. The activity of at least a RAB3B regulatory element operably linked to the reporter gene can then be directly observed and quantified as a function of reporter gene activity in a reporter gene assay. In one embodiment, for example, at least a RAB3B regulatory element could be cloned upstream from a luciferase reporter gene within a reporter vector. This could be introduced into the test cells, along with an internal control reporter vector (e.g., a lacZ gene under the transcriptional regulation of the β-actin promoter). After the cells are exposed to the test compounds, reporter gene activity is measured and the reporter gene activity is normalized to internal control reporter gene activity.

Example 1

RAB3B is more Highly Expressed in A10 DA Terminals Compared to A9 DA Terminals

DA neurons in the SN (A9) mainly project to the dorsal lateral striatum whereas DA neurons in the VTA (A10) innervate the medial ventral striatum, nucleus accumbens, septum, and cortex. It is known that RAB3 proteins are mainly enriched in synaptic terminals. Accordingly, histological sections of the normal rat brain containing the striatum, septum and nucleus accumbens were stained with RAB3A and RAB3B antibodies in order to determine the pattern of RAB protein localization in these forebrain structures innervated by the A9 and A10 DA neurons (Chung et al., J. Neurosci. 27: 8314-8323, 2007).

RAB3A and RAB3B showed very distinct expression patterns relative to each other. RAB3A was expressed evenly throughout the striatum and nucleus accumbens, not limited to DA terminals (FIGS. 1A and 1D). In contrast, RAB3B was expressed very highly in nucleus accumbens and septum and was enriched in mainly DA terminals of these areas (FIGS. 1B, 1C, 1E, and 1F). These results provide anatomical evidence that RAB3B is more expressed in the VTA (A10) dopaminergic neurons compared to the SN (A9) neurons.

In order to determine whether the differential expression pattern of RAB3B observed in rat is conserved in human, DA neurons from the SN (A9) and the VTA (A10) were collected in fresh frozen human midbrain sections using laser capture microdissection (LCM) (FIG. 1G-I). Brains were cut using a cryostat with 10 μm (for mouse) or 18 μm (for human) thickness, mounted on LCM slides (Arcturus) and immediately stored at −70° C. A quick TH immunostaining and LCM was performed accordingly to the previous protocol (Chung et al., Hum Mol Genet., 14: 1709-1725, 2005). Briefly, the tissue sections were fixed in cold acetone for 4 minutes, washed with PBS, incubated with rabbit anti-TH (Pel-Freez Biologicals, Rogers, Ark.; 1:25) for 4 min, washed in PBS, and exposed to biotinylated anti-rabbit antibody (Vector Laboratories, Burlingame, Calif.; I: 25) for 4 min. The slides were washed in PBS, incubated in ABC-horseradish peroxidase enzyme complex (Vectastain, Vector Laboratories) for 4 min and the staining was detected with the substrate, diaminobenzidine (DAB). Primary secondary and ABC solution contained RNase inhibitor (200 unit/ml). Sections were subsequently dehydrated in graded ethanol solution (30 sec each in water, 70% ethanol, 95% ethanol, 100% ethanol, and twice for 2 min in xylene). For LCM, the PixCell II System (Arcturus, Mountain View, Calif.) was used to capture approximately 100-200 neurons. RNA was isolated using PicoPure RNA isolation kit (Arcturus, Mountain View, Calif.). Quantitative PCR was performed according to previous protocol (Chung et al., Hum Mol Genet., 14: 1709-1725, 2005). Briefly, RNA samples from A9 and A10 DA neurons were reverse-transcribed into cDNA using Sensiscript reverse transcriptase (Qiagen, Valencia, Calif.) and oligo dT as the primer. PCR reactions were set up in 25 μl reaction volume using SYBR Green PCR Master Mix (Applied Biosystems, Foster City, Calif.) with 250 nM final concentrations of primers. For each primer pairs, triplicates of three to five independently collected A9 and A10 samples were compared to quantify relative gene expression differences between these cells using the $2^{-\Delta\Delta CT}$ method (Livak et al., Methods, 25(4):402-8, 2001). Beta-actin was used as an internal control gene. Quantitative PCR results for three isoforms of RAB3 (RAB3A, B and C), demonstrated that RAB3B mRNA was expressed at significantly higher levels in the VTA (A10) compared to the SN (A9); whereas, the mRNA expression of RAB3A and RAB3C was approximately equal between A9 and A10 DA neurons (FIG. 1J). Specifically, RAB3B mRNA was about 14-fold more highly expressed in A10 cells relative to A9 cells in both male and female subjects.

Example 2

RAB3B is Protective Against 6-OHDA and MG-132 Toxicity in BE(2)-M17 Cells

In order to investigate the role of RAB3B in neuroprotection, the human dopaminergic neuroblastoma cells line BE(2)-M17 ("M17 cells") was transduced with lentivirus carrying RAB3A (GenBank Accession Nos.: AF254795.1 (gene) and NP_002857 (protein)) or RAB3B (GenBank Accession Nos: AF498932.1 (gene) and NP_002858.2 (protein)) and GFP protein. This resulted in stable cell lines that overexpressed RAB3A or RAB3B.

Figure 2:
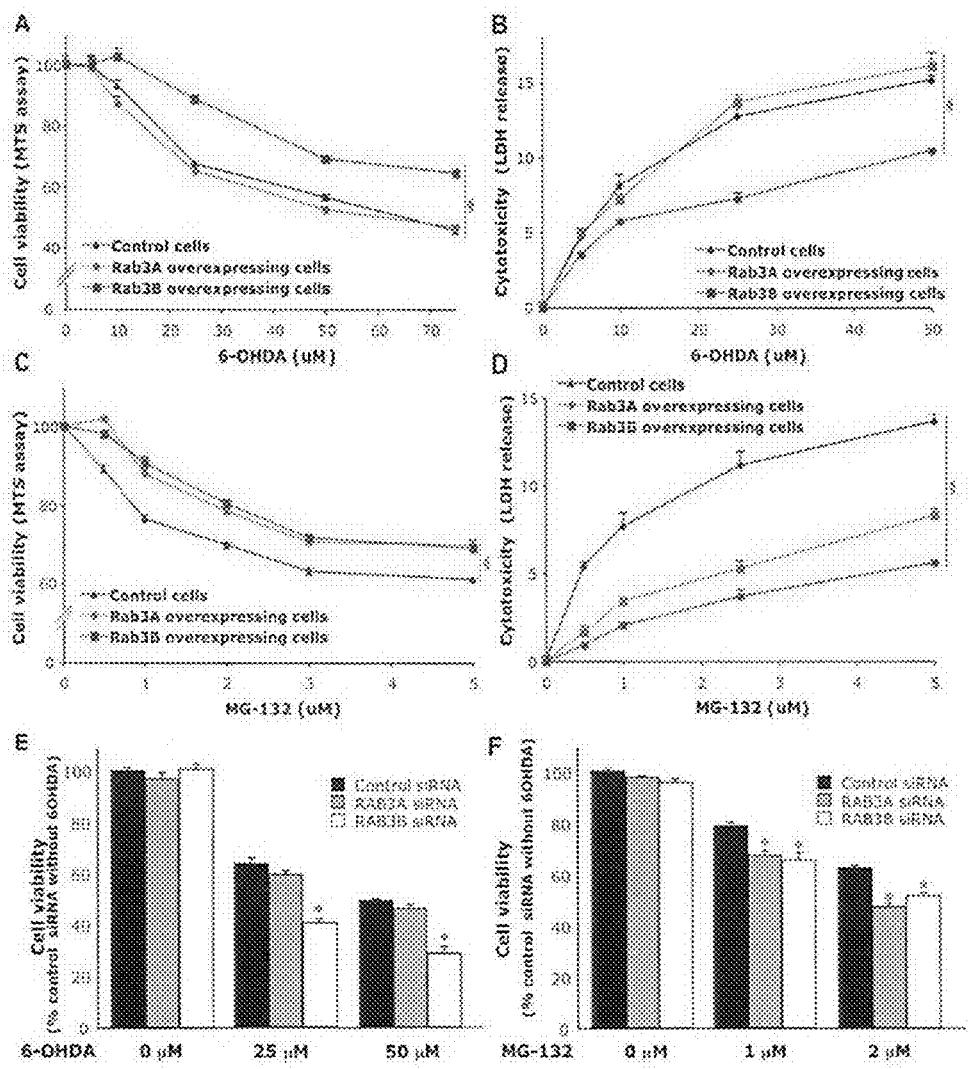
FIG. 2 shows that overexpression of RAB3B is protective against 6-OHDA and MG-132 toxicity in BE(2)-M17 cells. Lentivirus containing RAB3A or RAB3B gene were transduced to BE(2)-M17 cells with a multiplicity of infection of 30. After exposing these cells to 6-OHDA (FIG. 2A and FIG. 2B) or MG-132 (FIG. 2C and FIG. 2D), cell viability was measured using MTS assay (FIG. 2A and FIG. 2C) and cytotoxicity was measured via LDH release (FIG. 2B and FIG. 2D). Overexpression of RAB3B was protective against 6-OHDA and MG-132 toxicity whereas RAB3A was protective only against MG-132 toxicity. Data are shown as means±SEM (n=6-8) and are representatives of three or more experiments with the similar trends.

Viability of the M17 cells was assessed following exposure to two neurotoxins, each representing different aspects of PD pathology: 6-hydroxydopamine (6-OHDA) as a model of oxidative stress and MG-132 which induces proteasome inhibition. Cytotoxicity of M17 cells was determined using both cell viability (MTS) assays and LDH release. As shown in FIG. 2, RAB3B demonstrated significant neuroprotection of M17 cells to escalating doses of 6-OHDA compared to both control cells and cells transfected with RAB3A, as measured by cell viability (FIG. 2A) and LDH release (FIG. 2B). RAB3B overexpression also caused significant neuroprotection against MG-132 relative to control cells (FIGS. 2C-2D). RAB3A was equally effective as RAB3B, as measured by the MTS assay, but was less effective than RAB3B in reducing LDH release.

To further confirm the role of RAB proteins in neuroprotection, the endogenous levels of RAB3A and RAB3B were knocked down using siRNA. The siRNA sequences are as follows:

```
RAB3A: cccgtcacccttatttattat,    (SEQ ID NO: 8)
and

RAB3B: cagcactagactaacataaca.    (SEQ ID NO: 9)
```

Cells were plated in 96 well plates at 5000 per well with siRNAs and siPORT NeoFX transfection agent (Ambion, Austin, Tex.). After 48 hrs of incubation with siRNAs, 6-OHDA, MG-132 and MPP+ were applied to the cells. Cell viability and cytotoxicity was measured after 20 hrs of toxin exposure. M17 cells treated with RAB3B siRNA were significantly more vulnerability to 6-OHDA and MG-132 toxicity compared to those cells transfected with the control siRNA (FIGS. 2E-2F). In further accordance with the observations described above, reduction of endogenous RAB3A mRNA did not affect the sensitivity of M17 cells to 6-OHDA, but sensitivity to MG-132 was enhanced (FIGS. 2E-2F).

Together, these results demonstrate that RAB3B expression levels has a profound impact on the sensitivity of DA neurons to a variety of neurotoxic insults with mechanisms implicated in the pathogenesis of PD. This in vitro data demonstrating the neuroprotective effects of RAB3B is in accordance with the in vivo observations that RAB3B is expressed at high levels in the A10 DA neurons which are relatively spared in PD, and at relatively low levels in the A9 DA neurons which are lost in disproportionately high number in PD.

Construction of Lentiviral Vectors: The human RAB3A and RAB3B cDNAs were cloned into the lentiviral vector, pRRL.cPPT.PGK.W.Sin-18 vector (provided by Drs. R. Zufferey and D. Trono, University of Geneva, Switzerland) and confirmed by sequence analyses.

Production of Lentiviral Vectors and Cell Transduction: Lower titer lentivirus production for in vitro transdution was based on a previously described protocol (Chung, 2005). Briefly, 293T cells were transfected with four plasmids: pMDLg/pRRE (for gag and pol expression), pMD.G (for expression of the VSV-G env protein) and pRSV.Rev (for rev expression). The plasmids were co-transfected with the recombinant pRRL.cPPT.RAB3B.W.Sin-18 vector to produce rivarl transduction units. Virus supernatants were collected and filtered through a 0.2 μm filter and ultracentrifuged to obtain high concentrations of viral stocks. Virus titers were determined according to published protocols (90 by) measuring the viral capsid protein p24 by ELISA.

In Vitro Protection Assays: BE(2)-M17 cells were transduced with lentivirus expressing control, RAB3A, or RAB3B cDNA with a multiplicity of infection 15. Cells were grown in Optimem™ (Invitrogen, Calsbad, Calif.) supplemented with 10% heat-inactivated fetal calf serum (Hyclone, Logan, Utah), nonessential amino acid and sodium pyruvate. Cells were maintained at 37° C., in 5% $CO_2$ humid atmosphere. For the bioassay, cells were plated in 96 well plates at 5000 per well. The next day, cells were treated with various concentrations of 6-OHDA (Sigma) or MG-132 (Calbiochem) for 20 hrs. The supernatant was used to determine cytotoxicity using LDH release assay kit (Roche, Indianapolis, Ind.) and the cells remaining on the plate was used to determine cell viability using MTS based solution, CellTiter 96 AQueous One™ solution cell proliferation assay (Promega, Madison, Wis.).

siRNA transfection: The siRNAs for human RAB3A and RAB3B and a negative control siRNA, as described herein, were used. Cells were plated in 96 well plates at 5000 per well with siRNAs and siPORT NeoFX transfection agent (Ambion, Austin, Tex.). After 48 hrs of incubation with siRNAs, each of the toxicants (6-OHDA or MG-132) were applied to the cells. Cell viability and cytotoxicity was measured after 20 hrs of toxin exposure.

Example 3

RAB3B Overexpression Increases Dopamine Uptake in M17 Cells

It has been previously reported that RAB3A and RAB3B overexpression in PC12 cells results in increased [$^3$H]-norepinephrine uptake into these cells (Weber et al., J. Biol. Chem., 271: 6963-6971, 1996; Francis et al., J. Biol. Chem., 277: 7816-7823, 2002). In order to investigate whether RAB3B may be involved with the synaptic vesicle uptake and release machinery in DA neurons, [$^3$H]-dopamine ([$^3$H]-DA) uptake was measured in naïve and RAB3B-overexpressing M17 cells.

BE-M17 cells expressing GFP or RAB3B were plated into 12 well plates with a cell density of $2 \times 10^4$ cells per well. Two days after plating, cells were incubated for 10 min at room temperature in the flux solution pH 7.4 containing 10 mM HEPES, 130 mM NaCl, 1.3 mM KCl, 2.2 mM $CaCl_2$, 1.2 mM $MgSO_4$, 1.2 mM $KH_2PO_4$, 10 mM glucose, 25 nM $[^3H]$ DA in the absence or presence of 50 µM nomifensine. For the uptake assay after digitonin permeabilization, cells grown on 12 well plates were permeabilized in culture medium containing 20 mM digitonin for 10 min. Cells were washed and equilibrated in HTMS buffer (20 mM HEPES, 20 mM Tris-HCl, 6 mM $MgCl_2$, 0.3 M sucrose, 4 mM ATP, pH 7.4) for 10 min. After removing HTMS buffer, cells were incubated in HTMS buffer containing 25 nM $[^3H]$ DA in the presence or absence of 100 mM reserpine for 10 min at room temperature. After isotope uptake in regular or digitonin-permeabilized conditions, cells were washed in cold phosphate buffered saline for three times and lysed in 0.4 ml of 0.5 N NaOH followed by addition of 0.1 ml of 2 N HCl to neutralize pH. Protein concentrations were measured using BCA assay in order to normalize the flux value to total protein per well. Duplicates of 25 ml lysed samples were used to determine protein concentrations by BCA assay and remaining samples were mixed with scintillation cocktail for radioactivity measurement in Beckman LS6000 liquid scintillation counter.

Figure 3:
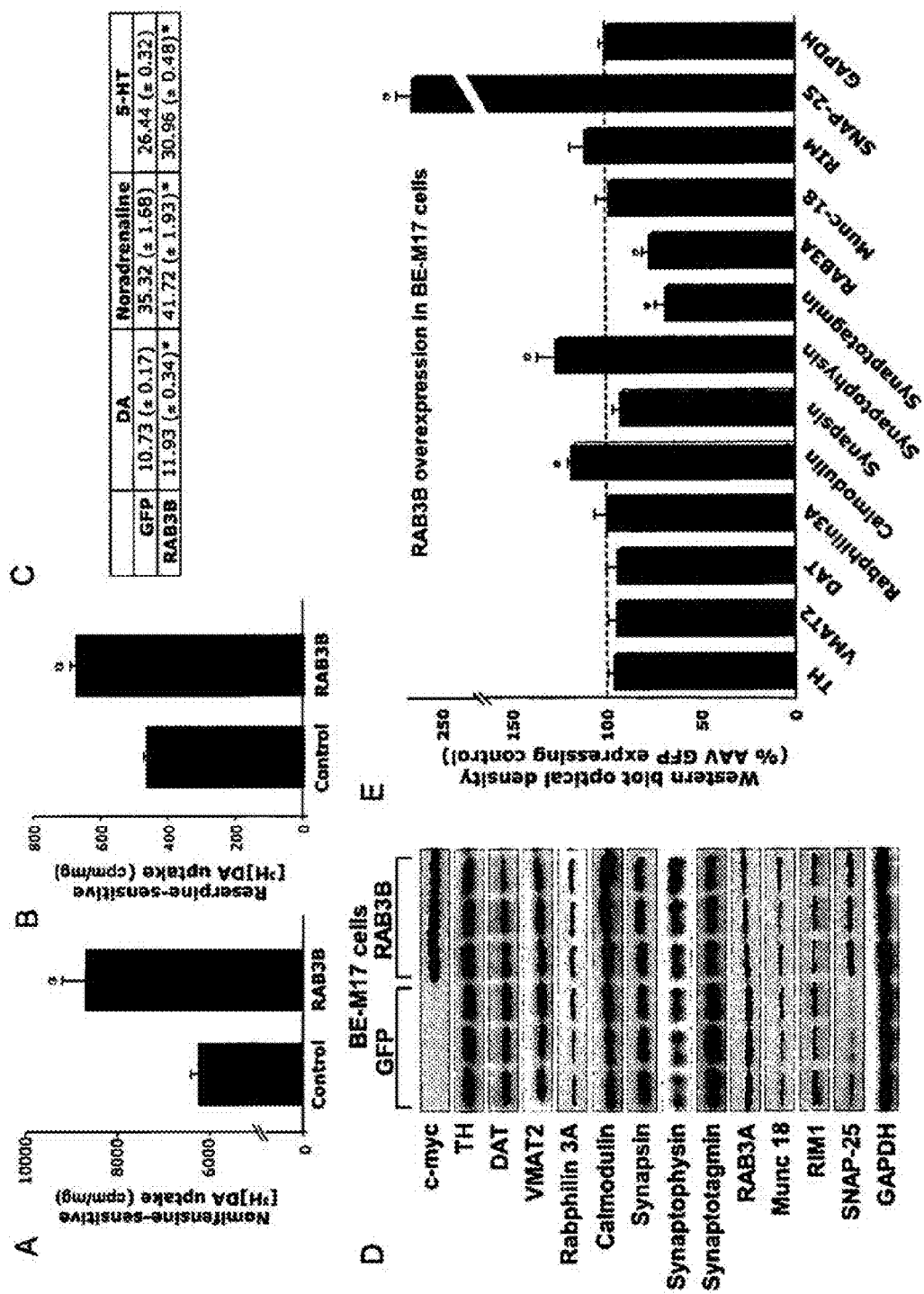
FIG. 3 shows that RAB3B overexpression in vitro increases levels of presynaptic proteins, [$^3$H] DA uptake, and DA content.

As shown in FIGS. 3A-3B, RAB3B overexpression resulted in a significant increase in both nomifensine-sensitive and reserpine-sensitive $[^3H]$-DA uptake. These results demonstrate that RAB3B enhances the functionality of the dopaminergic signaling mechanisms in neurons. In addition, RAB3B overexpression caused an increased in neurotransmitter content measured by HPLC, including DA, noradrenaline, and 5-HT (FIG. 3C). Levels of presynaptic proteins after overexpressing RAB3B in BE(2)-MI7 cells (FIGS. 2D and E) were analyzed by Western blot. RAB3B overexpression was confirmed in these cells by the increased levels of c-myc. Among known RAB3B effector proteins such as rabphilin 3A, calmodulin, synapsin and RIM1, only calmodulin levels were significantly increased after RAB3B overexpression (FIGS. 3D and E). Among other proteins localized in vesicles, levels of synaptophysin and SNAP-25 were significantly increased in these cells. Levels of synaptotagmin and RAB3A levels were reduced, suggesting that these proteins may have redundant functions to RAB3B or other presynaptic proteins increased by RAB3B overexpression. TH, DAT and VMAT2 levels remained unaltered.

Example 4

Adeno-Associated Viral Delivery of RAB3B into the Substantia Nigra Increases Striatal Dopamine Content and Synaptic Protein Levels The foregoing results clearly demonstrate that RAB3B provides significant neuroprotection in in vitro models of dopaminergic neuronal toxicity. To extend these findings, the neurobiological effect of RAB3B overexpression in the SN was investigated in naïve rats.

The rAAV-A53T-α-syn vector contains the coding sequence for the human α-syn gene under the control of the synapsin promoter. The AAV was prepared as detailed in previous manuscripts (Kirik et al., 2002; Maingay et al., 2006), except a synapsin promoter was used as opposed to a CBA promoter. rAAV vectors were packaged in AAV capsids, purified and tittered as previously described (Zolotukhin et al., 1999). The final titer for the vector encoding A53T-α-syn was $1.8 \times 10^{12}$ genome copies/ml, and GFP, $1.5 \times 10^{12}$ as determined by dot blot.

rAAV nigral injection: Animals received two 2.00 µl stereotaxic injections of rAAV-synapsin-GFP or A53T α-synuclein over the SN. The injections were given at a rate of 0.5 µl/min using microinfusion pumps (Stoelting Co, Wood Dale, Ill.), with a wait time of 10 min between injections. Stereotaxic coordinates for the surgeries were taken from the "Rat Atlas" by Paxinos and Watson (Paxinos, 1986). Prior to surgery, the animals were anesthetized with xylazine and ketamine (3 mg/kg and 60 mg/kg, respectively). The animals were placed in a stereotaxic frame (Stoelting, Wood Dale, Ill., USA) where a 10 µl Hamilton syringe was used as a delivery system. All injections were made into the substantia nigra using the following anteroposterior (AP), mediolateral (ML) and dorsoventral (DV) coordinates: first site, AP=−4.8 mm; ML=−2.0 mm; DV=−7.2 mm relative to dura, second site, AP=−5.5 mm; ML=−1.9 mm, DV=7.0 mm relative to dura; toothbar (TB) set at −2.3 mm. Solutions were injected at a rate of 0.5 µl/min and once the injection was completed, the needle was left in position for a further 10 min before being slowly retracted.

Immunoblotting: Cells and tissue samples were collected from and suspended in lysis buffer containing: 50 mM Tris-HCl, 0.15 M NaCl, 5.0 mM EDTA, and 1% Triton-X. In addition, phosphatase inhibitors I and II (1:100) and protease inhibitors (1:100) were added before homogenization (P2850, P5276, and P8340, respectively; Sigma). Following cell lysis, the homogenate was centrifuged, a portion of the supernatant was reserved for protein determination (BCA Assay, Pierce, Rockford, Ill.) and the remaining solution was stored at −20° C. 20 µg (in vitro cell preps) and 10-20 µg of proteins from the tissue preparations were used to run a gel. The respective volumes were mixed 1:1 with sample buffer and then boiled for 5 minutes. After boiling, the samples were loaded into the Criterion precast 4-15%, 10%, or 12.5% SDS polyacrylamide gel system (BioRad, Hercules, Calif.). After the electrophoresis was completed, the proteins were transferred from the gel to a PVDF membrane electrically at 80V for 1 hr. Then, the membranes were washed in Tris-buffered saline with 0.1% Tween 20 (TBS-T). After at least 1 hour of incubation, the membranes were incubated over night at 4° C. in various primary antibodies [c-myc (Novus, 1:1000), TH (Pel Freeze, 1:3000), Dopamine Transporter (DAT, Chemicon, 1:2000), Vesicular Monoamine Transporter 2 (VMAT2, Pel Freeze 1:1000), SNAP-25 (Chemicon, 1:4000), Rabphilin3A (BD transduction laboratory, 1:2000), RAB3A (Affinity Bioreagent, 1:3000), Synaptophysin (Santa Cruz, 1:500), Synaptotagmin (BD transduction laboratory, 1:5000), Synapsin (Chemicon, 1:5000), RIM (BD Transduction Laboratory, 1:2000), Munc-18 (Affinity Bioreagents, 1:3000), Calmodulin (Upstate, 1:2000) and GAPDH (Chemicon, 1:5000). After washing in TBS-T, the membranes were next incubated in HRP-conjugated secondary antibodies for 1 hour at room temperature, probed for immunoreactive bands through chemiluminescence (Amersham Biosciences, Arlington Heights, Ill.) and exposed to film using the Kodak Biomax film system. Optical density analysis (NIH Image) was used to determine the relative abundance of protein in each sample and this value was used in the statistical analyses.

It was found that AAV-RAB3B was transduced into TH-positive neurons to varying degrees depending upon the neuroanatomical level. The majority of the TH-positive neurons in the rostral SN were transduced with exogenous RAB3B, detected by c-myc immunofluorescence staining (FIGS. 4A-4D). The transduced DA neurons transported RAB3B to the synaptic terminals in the striatum, as evidenced by the presence of unilateral c-myc immunostaining in the transduced cerebral hemisphere (FIG. 4E).

Transduced and naïve rat striata were dissected and used for biochemical and protein analysis. As shown in FIG. 4F, RAB3B significantly increased the striatal DA content, but did not alter the ratio of DA/DA metabolites.

Since DA content measured by HPLC mainly account for vesicular DA, these results indicate that RAB3B overexpression led to increased vesicular DA content. These data are also consistent with findings in RAB3B overexpressing cells in vitro.

Extracellular DA and DOPAC levels in the striatum were measured, after challenging with 50 mg/kg L-DOPA administration using microdialysis. Such experiments showed no increase in baseline DA levels with or without intraperitoneal injection of L-DOPA (FIG. 4G). However, L-DOPA administration induced a marked increase in DOPAC levels from the baseline in the control striatum. In contrast, this surge of DOPAC increase was abolished in the RAB3B overexpressing striatum (FIG. 4H).

The RAB3B-mediated increase in striatal DA content by HPLC and the absence of DOPAC surge after L-DOPA by microdialysis, suggested at least two possibilites: 1) increased DA packing per vesicles, and/or 2) increased number of synaptic vesicles at presynaptic terminals. In order to address this issue, the number and the size of synaptic vesicles were quantified in GFP or c-myc (RAB3B)-positive presynaptic terminals using an electron microscopy combined with immunogold staining.

Electron Microscopy: Rats were perfused with 4% paraformaldehyde (pH 7.4) and 0.5% glutaraldehyde. Brains were vibrosliced with 40 μm thickness and stored in 30% sucrose PBS. Sections were osmicated with 1% osmium ferrocyanide, dehydrated, and embedded in Epon. High Osmium concentration used in our experiments increased the contrast of EM images, providing crisp images of synaptic vesicles. This, however, compromised the immunoreactivity of antigens that were used, causing fewer gold particles per presynaptic terminals (FIGS. 4I and J). Sections were mounted on uncoated Ni grids and pretreated with 1% sodium meta-periodate for 10 min. After four times of 5 min wash in PBS, sections were blocked for 1 hour (1% BSA. 10% goat serum, 0.1% fish gelatin and 0.02% Triton-X in PBS). Anti-GFP antibody (Invitrogen, 1:400) or anti-c-myc antibody (Novus, 1:300) were diluted in PBS containing 2% goat serum, 0.1% fish gelatin. Grids were incubated in the primary antibodies for overnight at room temperature. After 3 times of 5 min wash in PBS-BSA (0.5% BSA. 0.1% fish gelatin and 0.1% Tween 20 in PBS), grids were incubated in 10 nm gold conjugates (Ted Pella, 1:25) in PBS-BSA for 1 hour. Then, grids were washed using PBS-BSA with high NaCl (final conc. 150 mM) for two times and PBS for two times. Sections on grids were postfixed in 1% glutaraldehyde for 5 min and washed in ultra pure water for four times. To increase contrast, grids were incubated in Raynold's lead (3 min)-uranyl acetate (12 min)-Raynold's lead (7 min) before visualization. Images of immunogold-positive presynaptic terminals marked by postsynaptic density were captured (73 terminals for the GFP expressing striatum and 85 terminals for the RAB3B expressing striatum) by JEOL electron microscope located in McLean hospital core facility. All the vesicles in synaptic terminals were counted in a blind manner. The size of the vesicles was determined using Stereoinvestigator software. Briefly, contour of synaptic terminals was drawn and random areas were selected by fractionator and the size of the vesicle within the counting frame was determined using nucleator to obtain the averaged vesicle size in each terminal (73 terminals for the GFP expressing striatum and 85 terminals for the RAB3B expressing striatum).

In vivo Microdialysis: Three weeks after nigral injection of AAV2 GFP or RAB3B, a dialysis probes (3 mm membrane length, 0.24 mm external diameter, Cuprophane, 6 kDa cut-off, CMA-11; CMA/Microdialysis, Solna, Sweden) was attached to the stereotaxic frame and implanted into the striatum. The probe was implanted at coordinates AP −0.3, ML −3.7, DV −6.0 relative to bregma. Twenty-four hours after surgery, the dialysis probes were connected to a syringe pump and perfused with artificial cerebrospinal fluid (aCSF) (NaCl 147 mM, KCl 2.7 mM, $CaCl_2$ 1.2 mM, $MgCl_2$ 0.85 mM; CMA Microdialysis). To reliably determine the basal extra-cellular DA levels in the striatum of freely moving rats a quantitative 'low perfusion' rate microdialysis experiment was conducted (Gainetdinov et al., J Neurosci., 23(32):10265-73, 2003). After an equilibration period for at least 1 h, the perfusate was collected at a perfusion rate of 0.1 μl/min every 60 min into collection tubes containing 2 μl of 0.5 N Hydrochloric acid. To analyze the effects of L-DOPA on the extra-cellular DA levels in the striatum, a 'conventional' microdialysis method (perfusion flow rate 1 μl/min) in freely moving animals was employed 48 h after surgery (Gainetdinov et al., J Neurosci., 23(32):10265-73, 2003). In these experiments, dialysis probes were equilibrated for 1 h using 1 μl/min CSF perfusion and samples were collected every 15 min into collection tubes containing 2 μl of 1N Hydrochloric acid. At this perfusion rate, 4 samples were collected as baseline, 5 samples after i.p. injection of saline solution, 3 samples after i.p. injection of benserazide 15 mg/kg, and 12 samples after i.p. injection of L-DOPA 50 mg/kg.

When synaptic vesicles were counted in immunogold-positive presynaptic terminals for GFP or c-myc (RAB3B), RAB3B positive terminals showed significantly higher number of synaptic vesicles per terminals than GFP-positive terminals (FIG. 4K). When immunogold-positive terminals were sorted based on the number of synaptic vesicles, more RAB3B-positive terminals fell into bins with higher number of synaptic vesicles, showing a right shifted curve (FIG. 4L). Average vesicle size of a single presynaptic terminal was determined. RAB3B-positive terminals contained significantly larger vesicles compared to GFP-positive terminals (FIG. 4M). These results suggest that increased in striatal DA content by HPLC and the absence of DOPAC surge after L-DOPA challenge measured by microdialysis may be, at least in part, due to the increase in number and/or size of synaptic vesicles.

Presynaptic protein profiles determined by Western blot analysis revealed that TH and VMAT2 levels were significantly reduced in RAB3B overexpressing striatum (FIG. 4N and FIG. 4O). Consistent with the in vitro findings (FIGS. 3D and E), levels of calmodulin, synaptophysin and SNAP-25 were significantly increased in the RAB3B overexpressing striatum (FIG. 4N and FIG. 4O).

Example 5

RAB3B Reverses Neurochemical and Behavioral Effects Caused by a 6-OHDA Lesion

Retrograde 6-OHDA lesioning within the striatum is a well-established method of creating progressive degeneration of A9 DA neurons. The loss of TH immunoreactivity reflects actual loss of DA neurons (Sauer et al., Neuroscience, 59: 401-405, 1994).

The in vivo neuroprotective effects of RAB3B against 6-OHDA-induced toxicity was examined by injecting 6-OHDA into the striatum of rats three weeks after either RAB3B or a control gene (GFP) was delivered to the midbrain using the adeno-associated virus as described above.

Figure 5:
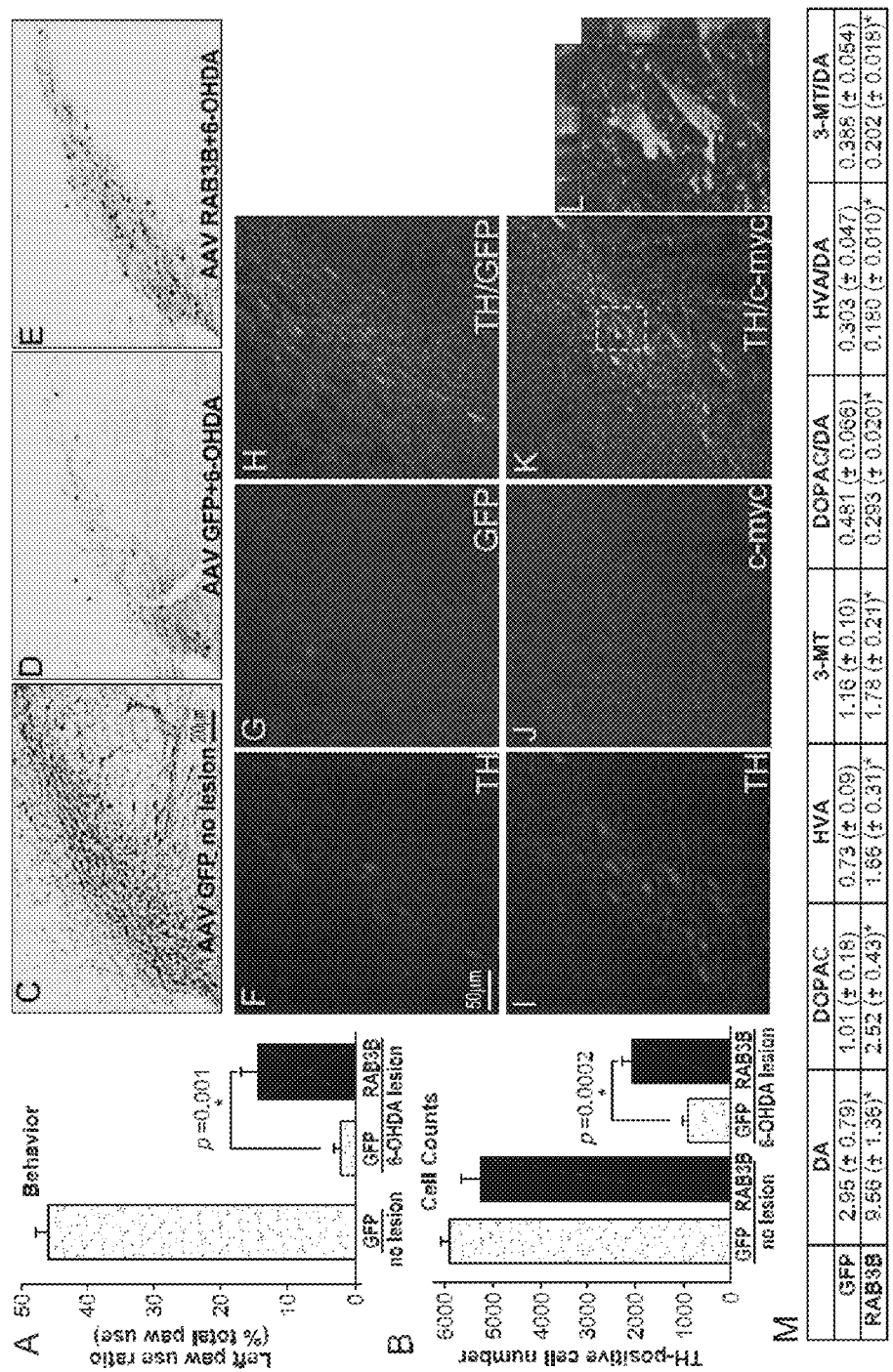
FIG. 5 shows that RAB3B overexpression protects DA neurons from a retrograde 6-OHDA lesion in rat. 6-OHDA was injected into the striatum 3 weeks after AAV GFP or RAB3B$^{c-myc}$ injection. Paw reaching test results showed that RAB3B overexpression improved the behavioral asymmetry caused by the 6-OHDA lesion (FIG. 5A). Data are shown as means±SEM (*; two tail t-test). TH-positive neurons in the SN were stained using DAB immunohistochemistry (FIG. 5B-E) and double immunofluorescent (GFP/TH or c-myc/TH) technique (FIG. 5F-L). Stereological counting demonstrated that more TH-positive neurons remained in the AAV RAB3B$^{c-myc}$ injected SN compared to the AAV GFP injected SN (Data are shown as means±SEM.*; two tail t-test). Most of the remaining TH-positive neurons in AAV RAB3B$^{c-myc}$ injected midbrain were strongly c-myc positive (FIG. 5I-K). Co-localization was confirmed by a z-stack image of the perforated square in FIG. 4K (FIG. 5L). HPLC analysis in the striatum after the 6-OHDA lesion, demonstrated that a significant increase in DA tissue content was measured in the RAB3B overexpressing striatum compared to the GFP expressing striatum (FIG. 5M). Ratios of DA metabolites to DA were reduced in the RAB3B overexpressing striatum (FIG. 5M). Data are shown as means±SEM (AAV GFP, n=12; AAV RAB3B$^{c-myc}$, n=12; *p<0.05 two tail t-test).

As a behavioural measurement, paw reaching preference was determined as a degree of asymmetry on ipsilateral (left in the present surgery paradigm) paw usage at three weeks after the 6-OHDA lesion. RAB3B overexpressing rats used left paws more frequently than GFP expressing rats, thus showing increased behavioral performance relative to the control group (FIG. 5A). In the postmortem analysis, stereological counting of TH-positive neurons showed that there were significantly more TH-positive neurons remaining in the RAB3B overexpressing SN compared to the GFP overexpressing SN after the 6-OHDA lesion (FIG. 5B-E). Most of the surviving TH positive neurons were strongly c-myc (or RAB3B)-positive (FIG. 5F-L), suggesting that RAB3B overexpression, not lesion variability, was the cause of their increased survival. Protection of SN (A9) DA neurons by RAB3B was also confirmed by increased DA content and reduced DA turnover in the RAB3B overexpressing striatum (FIG. 5M).

Animals: Female Sprague-Dawley rats weighing ~250 g (Charles River Laboratories) were used in all animal experiments. All rat studies were approved by the McLean Hospital Institutional Animal Care and Use Committee.

Stereotaxic SurgeryAll stereotaxic coordinates were derived from the Rats Atlas of Paxinos and Watson ("The Rat Brain in Stereotaxic Coordinates". Academic Press, San Diego, Calif., 1986). For each surgery animals were deeply anesthetized with ketamine and xylazine (60 mg/kg and 3 mg/kg respectively, i.m.).

Substantia Nigra Adeno-associated Viral Injection: Rats received unilateral injection of AAV2 GFP (titer: $1.5 \times 10^{12}$ genome copy per ml) or c-myc tagged RAB3B (titer: $2.8 \times 10^{12}$ genome copy per ml) virus above the SN. High titer AAV2 was produced by Harvard Gene Therapy Initiative. Synapsin, a neuron specific promoter was used for AAV2. Rats were anesthetized with ketamine and xylazine. Two µl of AAV2 was injected at two sites stereotaxically over the SN (site 1: 4.8 mm posterior (AP) and 2.0 mm lateral (ML) to bregma, 7.1 mm ventral to dura (DV), site 2: 5.5 mm posterior and 1.9 mm lateral to bregma, 7.0 mm ventral to dura). All injections were made using a continuous infusion system (Stoelting Co, Wood Dale, Ill.) that is attached to a 10 µl Hamilton microsyringe with 31-gauge needle. Injection rate was 0.5 µl/min and the needle was left in place for 10 min before it was slowly retracted from the brain.

6-OHDA Intra-striatal Injection: Three weeks following AAV injection, animals received three 2.5 µl stereotaxic injections of 3.0 µg/µl 6-OHDA (total dose=22.5 µg 6-OHDA) delivered at a rate of 0.5 µl/min and 5 min wait times after each injection. Striatum injection coordinates were as follows: site 1: AP +1.3, ML −2.8, DV −4.5; site 2: AP +0.2, ML, −3.0, DV −5.0; site 3: AP −0.6, ML −4.0, DV −5.5; and tooth bar set at −3.3. The lesion was allowed to progress for 3 weeks after which animals were sacrificed for post mortem analyses.

Paw reaching test. Animals were deprived from food over night and placed inside an 18-gallon cylinder (Nalgene, Rochester, N.Y.) between two mirrors set up at right angles to each other to facilitate scoring of movements made on sides of the cylinder not facing the observer. The rats were videotaped for 1 minute in the light and 1 minute in the dark immediately following placement. After the test, an observer scores each instance in which a rat begins, with all four paws, on the floor places one or both forelimbs on the wall of the cylinder. The score was recorded as the fraction of total contacts in which the paw contralateral to the lesion touched the wall first (Moore et al., Exp. Neurol., 172: 363-376, 2001).

Perfusions and Tissue Handling: Animals were deeply anesthetized with an i.p. injection sodium pentobarbital and were sacrificed by exsanguination with the aid of ice-cold saline perfusion. For immunohistochemistry, the brains were then fixed with a 4% paraformaldehyde solution. The brains were then removed from the skull and placed in fresh 4% paraformaldehyde solution for 2 h, and equilibrated through 20% and 30% sucrose solutions and refrigerated until cutting for immunohistochemistry. For immunoblotting and HPLC, brains were rapidly removed after heparin containing saline perfusion and sliced coronally using a tissue chopper set to 1 mm (Campden Instruments Ltd., Lafayette, Ind.). On an inverted glass Petri dish over ice, regions of interest (striatum and substantia nigra region) were dissected from the individual 1 mm tissue slices, frozen on dry ice, and stored at −80° C.

Immunohistochemistry: Brains were cut frozen in the coronal plane at a thickness of 40 µm on a sliding microtome and twelve series of sections were stored in cryoprotectant. Two full series of sections were processed for visualization of Tyrosine hydroxylase (TH) via the biotin-labeled antibody procedure. Briefly, following several washes in a PBS solution containing 0.02% Triton X-100 (PBS-T), endogenous peroxidase was quenched in a 3% hydrogen peroxide solution and background staining was then inhibited in a 10% normal goat serum solution. Tissue was then incubated with rabbit anti-TH antibody overnight (1:1000, Pel-Freez, Rogers, Ark.) and rabbit ant-myc antibody (:3000, Novus). After three washes in PBS-T, sections were sequentially incubated in biotinylated goat anti-rabbit IgG (1:300; Vector, Burlingame, Calif.) for 1 h and the Elite™ avidin-biotin complex (ABC Kits™; Vector, Burlingame, Calif.) for 1 h separated by three washes in PBS. TH immuno staining was visualized following a reaction with 3,3-diaminobenzidine (Vector). Sections were then mounted on glass slides, allowed to dry, dipped into $dH_2O$, dehydrated through graded alcohol (70%, 95%, 100%), cleared in xylenes, and coverslipped with DPX mounting medium. For immunofluorescence staining, sections were washed with PBS-T and blocked with donkey serum. Sections were then incubated with anti-TH (1:1000, Pel-Freez), RAB3A (1:1000, Affinity Reagents) or RAB3B (1: 1000, custom made), anti-eGFP (Chemicon), and anti-c-myc (Affinity Bioreagents) antibodies overnight and subsequently incubated in the following fluorophore-conjugated secondary antibodies: Alexa 488 (to visualize eGFP), Alexa 568 (to visualize TH), and Alexa 647 (to visualize G-substrate) (Invitrogen, Carlsbad, Calif.). Sections were mounted onto glass slides and visualized using confocal microscopy.

Cell Counting: Estimates of TH-positive neuronal number within the SN were performed using Stereo Investigator™ software (MBF Bioscience, Williston, Vt.) and stereologic principles (West et al., J. Comp. Neurol. 296: 1-22, 1990). The anterior and posterior boundaries of the SN included in the analysis were defined according to the area transduced by lenti-eGFP in preliminary experiments (approximately −4.80 mm through −6.00 mm from Bregma, according to the rat brain atlas of Paxinos and Watson). Stereology was performed using a Zeiss Axiovert microscope (Zeiss, Thornwood, N.Y.) coupled to an Optronics Microfire digital camera (Goleta, Calif.) for visualization of tissue sections. The total number of TH-positive neurons, from tissue sections separated by 120 µm, was estimated from coded slides using the optical fractionator method. For each tissue section analyzed, section thickness was assessed empirically and guard zones of 2 µm thickness were used at the top and bottom of each section. The SN was outlined under low magnification (2.5×) and approximately 50% of the outlined region was analyzed using a systematic random sampling design generated with the following stereologic parameters: grid size, 200×200 µm; counting frame size, 153×140 µm; and dissector height, 16 µm. Neurons were counted under 40× magnification. The coefficients of error (CE) were calculated according to the procedure of Gundersen et al., values <0.10 were accepted.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Other embodiments are within the claims.

SEQUENCE LISTING

The instant application contains a Sequence Listing which has been submitted via EFS-Web and is hereby incorporated by reference in its entirety. Said ASCII copy, created on Aug. 4, 2009, is named 08388308.txt and is 5 kilo bytes in size.

What is claimed is:

1. A method for increasing dopaminergic neuron content in the brain of a human patient affected with Parkinson's Disease, said method comprising administering with a stereotactic injection into the substantia nigra and/or ventral tegmental region comprising A9 neurons of the patient's brain an adeno associated virus vector comprising a polynucleotide encoding human RAB3B having the sequence set forth in SEQ ID NO: 6, wherein the human RAB3B is expressed and wherein the expression results in increase of dopaminergic neuron content.

2. The method of claim 1, wherein said substantia nigra region is substantia nigra A9 region comprising A9 neurons.

3. The method of claim 1, wherein said polynucleotide encoding human RAB3B is operably linked to at least one regulatory element.

4. The method of claim 1, wherein the stereotactic injection is performed as intracerebroventricular injection.

5. The method of claim 1, wherein the stereotactic injection is performed as intranigral injection.

6. The method of claim 3, wherein the adeno-associated virus is AAV2.

* * * * *

SEQUENCE LISTING

```
<160> NUMBER OF SEQ ID NOS: 11

<210> SEQ ID NO 1
<211> LENGTH: 219
<212> TYPE: PRT
<213> ORGANISM: Homo sapiens

<400> SEQUENCE: 1

Met Ala Ser Val Thr Asp Gly Lys Thr Gly Val Lys Asp Ala Ser Asp
1               5                  10                  15

Gln Asn Phe Asp Tyr Met Phe Lys Leu Leu Ile Ile Gly Asn Ser Ser
            20                  25                  30

Val Gly Lys Thr Ser Phe Leu Phe Arg Tyr Ala Asp Asp Thr Phe Thr
        35                  40                  45

Pro Ala Phe Val Ser Thr Val Gly Ile Asp Phe Lys Val Lys Thr Val
    50                  55                  60

Tyr Arg His Glu Lys Arg Val Lys Leu Gln Ile Trp Asp Thr Ala Gly
65                  70                  75                  80

Gln Glu Arg Tyr Arg Thr Ile Thr Thr Ala Tyr Tyr Arg Gly Ala Met
                85                  90                  95

Gly Phe Ile Leu Met Tyr Asp Ile Thr Asn Glu Glu Ser Phe Asn Ala
            100                 105                 110

Val Gln Asp Trp Ala Thr Gln Ile Lys Thr Tyr Ser Trp Asp Asn Ala
        115                 120                 125

Gln Val Ile Leu Val Gly Asn Lys Cys Asp Met Glu Glu Arg Val
    130                 135                 140

Val Pro Thr Glu Lys Gly Gln Leu Leu Ala Glu Gln Leu Gly Phe Asp
145                 150                 155                 160

Phe Phe Glu Ala Ser Ala Lys Glu Asn Ile Ser Val Arg Gln Ala Phe
                165                 170                 175

Glu Arg Leu Val Asp Ala Ile Cys Asp Lys Met Ser Asp Ser Leu Asp
            180                 185                 190

Thr Asp Pro Ser Met Leu Gly Ser Ser Lys Asn Thr Arg Leu Ser Asp
        195                 200                 205

Thr Pro Pro Leu Leu Gln Gln Asn Cys Ser Cys
    210                 215

<210> SEQ ID NO 2
<211> LENGTH: 8
<212> TYPE: PRT
<213> ORGANISM: Homo sapiens

<400> SEQUENCE: 2
```

```
Gly Asn Ser Ser Val Gly Lys Thr
1               5

<210> SEQ ID NO 3
<211> LENGTH: 5
<212> TYPE: PRT
<213> ORGANISM: Homo sapiens

<400> SEQUENCE: 3

Asp Thr Ala Gly Gln
1               5

<210> SEQ ID NO 4
<211> LENGTH: 4
<212> TYPE: PRT
<213> ORGANISM: Homo sapiens

<400> SEQUENCE: 4

Asn Lys Cys Asp
1

<210> SEQ ID NO 5
<211> LENGTH: 9
<212> TYPE: PRT
<213> ORGANISM: Homo sapiens

<400> SEQUENCE: 5

Phe Val Ser Thr Val Gly Ile Asp Phe
1               5

<210> SEQ ID NO 6
<211> LENGTH: 660
<212> TYPE: DNA
<213> ORGANISM: Homo sapiens

<400> SEQUENCE: 6
atggcttcag tgacagatgg taaaactgga gtcaaagatg cctctgacca gaattttgac      60
tacatgttta aactgcttat cattggcaac agcagtgttg gcaagacctc cttcctcttc     120
cgctatgctg atgacacgtt caccccagcc ttcgttagca ccgtgggcat cgacttcaag     180
gtgaagacag tctaccgtca cgagaagcgg gtgaaactgc agatctggga cacagctggg     240
caggagcggt accggaccat cacaacagcc tattaccgtg gggccatggg cttcattctg     300
atgtatgaca tcaccaatga agagtccttc aatgctgtcc aagactgggc tactcagatc     360
aagacctact cctgggacaa tgcacaagtt attctggtgg ggaacaagtg tgacatggag     420
gaagagaggg ttgttcccac tgagaagggc cagctccttg cagagcagct tgggtttgat     480
ttctttgaag ccagtgcaaa ggagaacatc agtgtaaggc aggcctttga gcgcctggtg     540
gatgccattt gtgacaagat gtctgattcg ctggacacag accgtcgat gctgggctcc     600 tccaagaaca cgcgtctctc ggacaccca ccgctgctgc agcagaactg ctcatgctag     660

<210> SEQ ID NO 7
<211> LENGTH: 9
<212> TYPE: DNA
<213> ORGANISM: Homo sapiens

<400> SEQUENCE: 7 rggcgkggc                                                               9

<210> SEQ ID NO 8
<211> LENGTH: 21
<212> TYPE: DNA
```

```
<213> ORGANISM: Homo sapiens

<400> SEQUENCE: 8
cccgtcaccc ttatttatta t                                              21

<210> SEQ ID NO 9
<211> LENGTH: 21
<212> TYPE: DNA
<213> ORGANISM: Homo sapiens

<400> SEQUENCE: 9
cagcactaga ctaacataac a                                              21

<210> SEQ ID NO 10
<211> LENGTH: 8
<212> TYPE: DNA
<213> ORGANISM: Homo sapiens

<400> SEQUENCE: 10 tgacataa                                                              8

<210> SEQ ID NO 11
<211> LENGTH: 9
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, c, g, t, unknown or other

<400> SEQUENCE: 11 rggcgggny                                                             9
```